US010730913B1

(12) United States Patent
Del Valle et al.

(10) Patent No.: US 10,730,913 B1
(45) Date of Patent: **\*Aug. 4, 2020**

(54) ANTIMICROBIAL ANALOGUES OF GRAMICIDIN S

(71) Applicants: Juan R. Del Valle, Tampa, FL (US); Lindsey Shaw, Tampa, FL (US)

(72) Inventors: Juan R. Del Valle, Tampa, FL (US); Lindsey Shaw, Tampa, FL (US)

(73) Assignee: University of South Florida, Tampa, FL (US)

( \* ) Notice: Subject to any disclaimer, the term of this patent is extended or adjusted under 35 U.S.C. 154(b) by 0 days.

This patent is subject to a terminal disclaimer.

(21) Appl. No.: 16/428,477

(22) Filed: May 31, 2019

Related U.S. Application Data

(63) Continuation of application No. 16/234,880, filed on Dec. 28, 2018, now Pat. No. 10,351,602.

(60) Provisional application No. 62/678,591, filed on May 31, 2018.

(51) Int. Cl.
| | | |
|---|---|---|
| C07K 7/66 | (2006.01) | |
| A61P 31/04 | (2006.01) | |
| A61P 31/10 | (2006.01) | |
| A61K 38/00 | (2006.01) | |

(52) U.S. Cl.
CPC ............... *C07K 7/66* (2013.01); *A61P 31/04* (2018.01); *A61P 31/10* (2018.01); *A61K 38/00* (2013.01)

(58) Field of Classification Search
CPC . C07K 7/66; A61P 31/10; A61P 31/04; A61K 38/00
See application file for complete search history.

(56) References Cited

U.S. PATENT DOCUMENTS

| | | |
|---|---|---|
| 4,554,101 A | 11/1985 | Hopp |
| 6,726,918 B1 | 4/2004 | Wong et al. |
| 8,043,628 B2 | 10/2011 | Wong |
| 8,778,999 B2 | 7/2014 | Hosseini et al. |
| 9,012,437 B2 | 4/2015 | Wong et al. |
| 9,592,242 B2 | 3/2017 | Wong |

OTHER PUBLICATIONS

Pal et al. Recent Studies on Gramicidin S Analog Structure and Antimicrobial Activity. Top Heterocyl Chem, vol. 49, pp. 159-202. (Year: 2017).*
Sarnowski et al. Peptide N-Amination Supports b-Sheet Conformations. Angew. Chem. Int. Ed. vol. 56, pp. 2083-2086. (Year: 2017).*
Berditsch et al. Therapeutic Potential of Gramicidin S in the Treatment of Root Canal Infections.Pharmaceuticals. vol. 9, No. 56, pp. 1-14. (Year: 2016).*
Lee et al. Structure-Activity Relationships of de-Novo Designed Cyclic Antimicrobial Peptides Based on Gramicidin S.Antimicrobial Peptides. Biopolymers (Peptide Science), vol. 71, pp. 28-48. (Year: 2003).*
Liu et al. Hydrazone and Hydrazide-Containing N-Substituted Glycines as Peptoid Surrogates for Expedited Library Synthesis: Application to the Preparation of Tsg101-Directed HIV-1 Budding Antagonists. Org Lett, 2006, vol. 8, No. 22, pp. 5165-5168. (Year: 2006).*
Lee, et al., "Structure-activity relationships of de novo designed cyclic antimicrobial peptides based on gramicidin S", Peptide Science vol. 71, Issue 1 2003, pp. 28-48.
Ruden, Serge, et al. "Synergistic interaction between silver nanoparticles and membrane-permeabilizing antimicrobial peptides." Antimicrobial agents and chemotherapy 53.8 (2009): 3538-3540.
Berditsch et al. Therapeutic Potential of Gramicidin S in the Treatment of Root Canal Infections. Pharmaceuticals (Basel), Sep. 2016, vol. 9, No. 56, pp. 1-14. (Year: 2016).
Fleeman et al., "Combinatorial Libraries as a Tool for the Discovery of Novel, Broad-Spectrum Antibacterial Agents Targeting the ESKAPE Pathogens," Journal of Medicinal Chemistry, 2015, 58, 3340-3355.
Gao et al., "Synthesis and screening of stereochemically diverse combinatorial libraries of peptide tertiary amides," Chem. Biol., 2013, 20(3): 360.
Heagerty et al., "Time-dependent ROC curves for censored survival data and a diagnostic marker," Biometrics, 2000, 56(2):337-344.
IUPAC 1974 Recommendations for Section E, Fundamental Stereochemistry, in Pure Appl. Chem., 1976, 45: 13-30.
Kang et al., "Solid-phase synthesis of tetrahydropyridazinedione-constrained peptides," Org. Lett., 2014, 5434.
Kang et al., "β-Strand mimics based on tetrahydropyridazinedione (tpd) peptide stitching," Chem. Commum., 2015, 16259.
Kyte et al., "A Simple Method for Displaying the Hydropathic Character of a Protein," J. Mol. Biol. 1982, 157, 105-132.
Li et al., "Dissociation of Antimicrobial and Hemolytic Activities of Gramicidin S through N-Methylation Modification," ChemMedChem, 2013, 8, 1865-1872.
Liu et al., "Hydrazone and Hydrazide-Containing N-Substituted Glycines as Peptoid Surrogates for Expedited Library Synthesis: Application to the Preparation of Tsg101-Directed HIV-1 Budding Antagonists," Org. Lett., 2006, 8(22): 5165.
Luo et al., "Inhibiting and Reversing Amyloid-β Peptide (1-40) Fibril Formation with Gramicidin S and Engineered Analogues," Chem. Eur. J., 2013, 19(51): 17338-17348.
McDermott et al., "N-Methylamino Acids in Peptide Synthesis. IV. Racemization and Yields in Peptide-bond Formation," Can. J. Chem., 1973, 51(15): 2562.
Pal et al., "Recent Studies on Gramicidin S Analog Structure and Antimicrobial Activity," Top. Heterocycl. Chem., 2017, 159-202.
Rathman et al., "Backbone Animated Gramicidin S Analogues with Enhanced Antimicrobial Activity," Poster, May 4, 2018.
Sarma et al., "Acyl hydrazides as peptoid sub-monomers," Chem. Commum., 2011, 47(38): 10590.

(Continued)

*Primary Examiner* — Marcela M Cordero Garcia
(74) *Attorney, Agent, or Firm* — Meunier Carlin & Curfman LLC

(57) ABSTRACT

Disclosed herein are N-aminated variants of Gramicidin S and methods of using the same for treating infections in a subject.

20 Claims, 5 Drawing Sheets

(56) References Cited

OTHER PUBLICATIONS

Sarma et al., "Submonomer synthesis of a hybrid peptoid-azapeptoid library," ACS Comb. Sci., 2012, 14(10): 558.
Sarnowski et al., "Peptide N-Amination Supports β-Sheet Conformations," Angew. Chem. Int. Ed., 2017, 56(8): 2083-2086.
Non-Final Office Action issued for U.S. Appl. No. 16/234,880, dated Apr. 12, 2019.
Notice of Allowance issued for U.S. Appl. No. 16/234,880, dated May 20, 2019.
Non-Final Office Action issued for U.S. Appl. No. 16/428,469, dated Jul. 5, 2019.

* cited by examiner

ANTIMICROBIAL ANALOGUES OF GRAMICIDIN S

CROSS-REFERENCE TO RELATED APPLICATIONS

This application is a divisional and claims the benefit of and priority to U.S. application Ser. No. 16/234,880, filed Dec. 28, 2018, which claims the benefit of and priority to U.S. Provisional Patent Application No. 62/678,591, filed on May 31, 2018, the entire contents of which are incorporated herein by reference in its entirety.

STATEMENT REGARDING FEDERALLY SPONSORED RESEARCH

This invention was made with government support CHE1709927 awarded by the National Science Foundation. The Government has certain rights in the invention.

TECHNICAL FIELD

The present disclosure relates to the synthesis and development of backbone N-aminated variants of Gramicidin S and therapeutic uses thereof.

BACKGROUND

The emergency of multi-drug resistant bacteria represents an ongoing public health crisis. β-Sheet antimicrobial peptides (AMPs) are a class of host defense peptides that potently inhibit the growth of Gram-positive and Gram-negative bacteria and are thus promising candidates for the treatment of multidrug-resistant bacterial infections. Gramicidin S (GS) is a naturally occurring AMP produced by *Bacillus brevis* that possesses antimicrobial activity against gram-positive and gram negative bacteria as well as fungi. While GS is very potent, it also causes hemolysis of human erythrocytes resulting in high levels of toxicity. Therefore, methods for reducing toxicity of GS are needed.

SUMMARY

In one aspect, disclosed are compounds of formula (I), a pharmaceutically acceptable salt thereof, wherein $R^1$, $R^2$, $R^3$, and $R^4$, are each independently selected from hydrogen or —$NH_2$.

At least one of $R^1$, $R^2$, $R^3$, and $R^4$ may be —$NH_2$. For example, $R^3$ may be —$NH_2$. As another example, $R^4$ may be —$NH_2$. At least two of $R^1$, $R^2$, $R^3$, and $R^4$ may be —$NH_2$. For example, $R^1$ and $R^3$ may be —$NH_2$. $R^3$ and $R^4$ may be —$NH_2$. $R^2$ and $R^3$ may be —$NH_2$. $R^2$ and $R^4$ may be —$NH_2$. At least three of $R^1$, $R^2$, $R^3$, and $R^4$ may —$NH_2$. For example, $R^1$, $R^3$, and $R^4$ may be —$NH_2$. $R^2$, $R^3$, and $R^4$ may be —$NH_2$. Each of $R^2$, $R^3$, and $R^4$ may be —$NH_2$.

Further disclosed herein are compositions comprising the compounds, and methods of treating infection in a subject using the compounds and compositions.

Other aspects and embodiments of the disclosure will become apparent in light of the following description and drawings.

DETAILED DESCRIPTION

Figure 1:
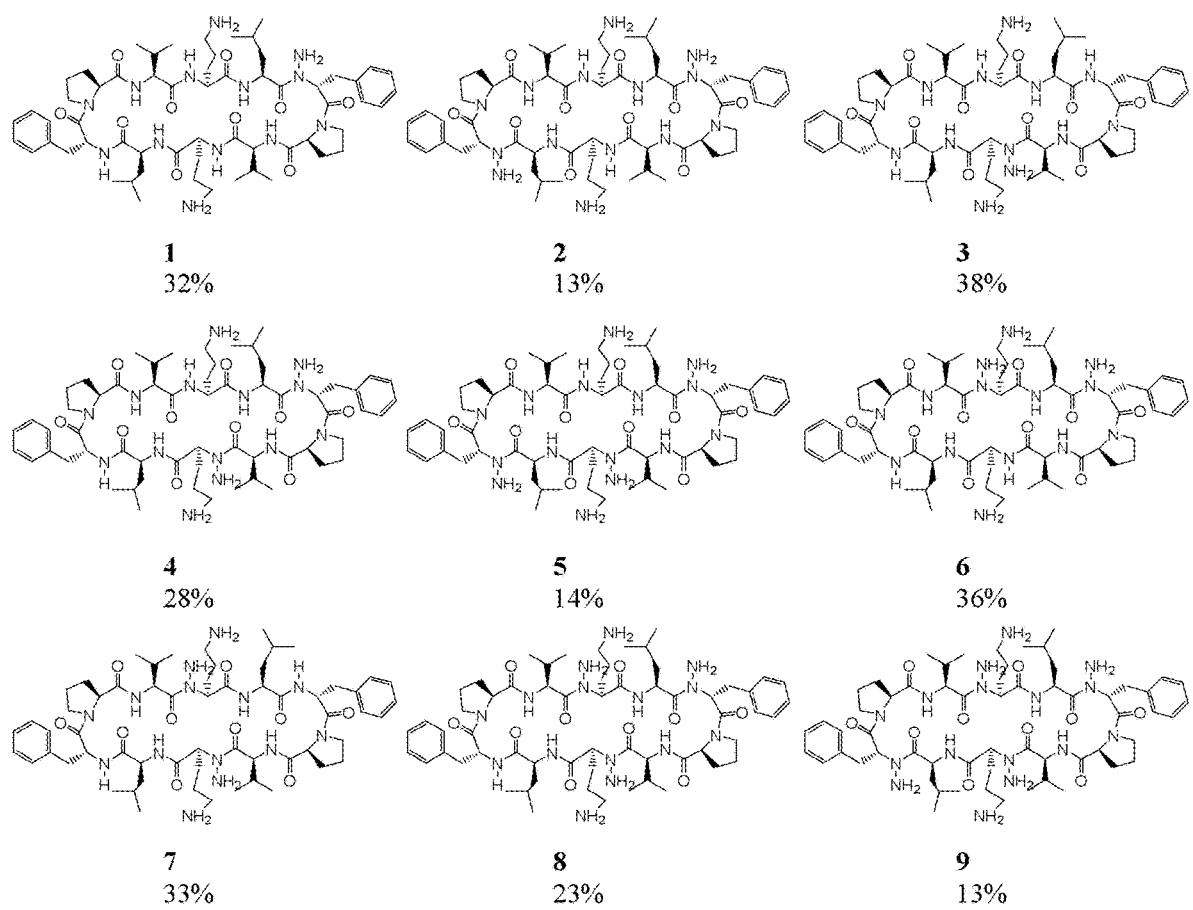
FIG. 1 shows representative compounds of formula (I).

Gramicidin S (GS) is a naturally occurring AMP produced by *Bacillus brevis* that possesses antimicrobial activity against gram-positive and gram negative bacteria as well as fungi. The potent antimicrobial activity of GS may result from disruption of the lipid membrane, resulting in enhanced permeability of the cell membrane and subsequent cell lysis. While GS displays potent antimicrobial activity, it also disrupts the cytoplasmic membrane of mammalian (i.e., non-bacterial) cells, resulting in hemolysis even at low concentrations. As such, methods to improve the selectivity of GS for bacterial over mammalian cells are needed.

The disclosure provides N-aminated analogues of GS. The analogues display improved antimicrobial activity and reduced hemolytic activity compared to naturally occurring GS.

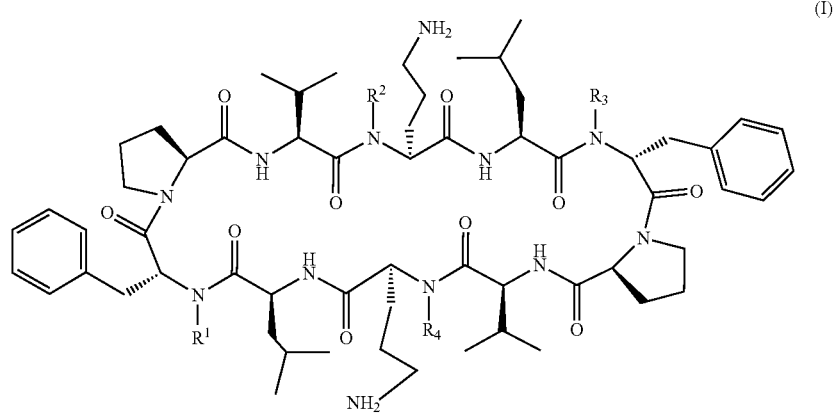

(I)

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

As used herein, the term "agonist" refers to a molecule or compound that triggers (e.g., initiates or promotes), partially or fully enhances, stimulates, or activates one or more biological activities. An agonist may mimic the action of a naturally occurring substance. Whereas an agonist causes an action, an antagonist blocks the action of the agonist.

The term "amination" as used herein refers to the process in which an amine group is added to a molecule. For example, when a bond is formed between a nitrogen atom in the molecule and the amino group the molecule is "N-aminated." Amination can occur in a number of ways including reaction with ammonia or another amine such as in an alkylation, reductive amination, electrophilic amination and the Mannich reaction or enzymatically by aminases.

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

The term "antagonist" or "inhibitor" refers to a molecule which blocks (e.g., reduces or prevents) a biological activity.

The term "antimicrobial" or "antimicrobial agent" as used interchangeably herein refers to an agent that kills microorganisms or stops the growth of microorganisms. Antimicrobial agents may be grouped according to the microorganisms that they act primarily against. Antimicrobial agents include, for example, antibiotic agents, antifungal agents, antiviral agents, and antiparasitic agents.

The terms "composition", "compositions", "pharmaceutical composition", and "pharmaceutical compositions" are used interchangeably herein to refer to a composition comprising the disclosed compounds.

The terms "control," "reference level," and "reference" are used herein interchangeably. The reference level may be a predetermined value or range, which is employed as a benchmark against which to assess the measured result. "Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty et al. (*Biometrics* 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, UK; StataCorp LP, College Station, Tex.; SAS Institute Inc., Cary, N.C.). The healthy or normal levels or ranges for a target or for a protein activity may be defined in accordance with standard practice. A control may be an subject or cell without a compound as detailed herein. A control may be a subject, or a sample therefrom, whose disease state is known. The subject, or sample therefrom, may be healthy, diseased, diseased prior to treatment, diseased during treatment, or diseased after treatment, or a combination thereof.

"Gram positive" is a taxonomic feature referring to bacteria which take up standard crystal violet primary Gram-staining dye. Gram staining is a process that differentiates bacteria by the chemical and physical properties of their cell walls by detecting peptidoglycan, which is present in the cell walls of gram-positive bacteria. Gram-positive bacteria may have more extensive peptidoglycan crosslinking in their cell walls than gram-negative bacteria.

"Gram-negative" is a taxonomic feature referring to bacteria which do not take up standard crystal violet primary Gram-staining dye. Peptidoglycan is typically present in a small layer in the cell walls of gram-negative bacteria. This small layer is easily dissolved with certain organic solvents such as, for example, ethanol or acetone, thus preventing the cell from retaining the violet primary stain. Gram-negative cells may be characterized by their cell envelopes, which are composed of a thin peptidoglycan cell wall sandwiched between an inner cytoplasmic cell membrane and a bacterial outer membrane. The ability of bacteria to retain or resist staining generally reflects the structure of the cell wall, and it has been suggested that Gram-positive bacteria have more extensive peptidoglycan crosslinking and less permeable cell walls than their Gram-negative counterparts.

The terms "microorganism" or "microbe" as used interchangeably herein refer to a unicellular or multi-cellular microscopic or macroscopic life form. Microorganisms include, for example, bacteria, protobacteria, phytoplankton, fungi, viruses, algae, molds, oomycetes, parasites, nematodes, and protozoans, or any combination thereof. Bacteria include Gram-negative bacteria, Gram-positive bacteria, aerobic bacteria, anaerobic bacteria, sulfate-reducing bacteria, nitrate-reducing bacteria, or any combination thereof. Bacteria may include pathogenic bacteria, which can cause an infection or a pathological condition in a subject.

"Minimal inhibitory concentration" or "MIC" refers to the minimum concentration, usually in micrograms per milliliter, of an antimicrobial agent at which no microbial growth is observed. At concentrations below the MIC, the antimicrobial agent is ineffective at killing or inhibiting the growth and reproduction of microbes. At concentrations above the MIC, the antimicrobial agent is effective at killing or inhibiting the growth and reproduction of microbes.

"Multidrug-resistant" refers to microbes which are resistant to multiple antimicrobial agents. For example, multidrug resistant bacteria may be resistant to multiple antibiotics.

The terms "naturally occurring GS" or "unmodified GS" as used interchangeably herein refers to GS that does not possess the N-amine modification.

The terms "N-aminated GS", "N-aminated analogues of GS", or "N-aminated analogues" are used interchangeably herein to refer to GS that has been aminated on one or more nitrogen atoms. N-aminated GS analogues may display one or more improvements over naturally occurring GS. For example, N-aminated GS analogues may display enhanced antimicrobial activity and/or reduced hemolytic activity compared to naturally occurring GS.

A "pharmaceutically acceptable excipient," "pharmaceutically acceptable diluent," "pharmaceutically acceptable carrier," or "pharmaceutically acceptable adjuvant" as used interchangeably herein means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use, such as those promulgated by the United States Food and Drug Administration.

"Polynucleotide" as used herein can be single stranded or double stranded, or can contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including, for example, uracil, adenine, thymine, cytosine, guanine, inosine, xanthine hypoxanthine, isocytosine, and isoguanine. Polynucleotides can be obtained by chemical synthesis methods or by recombinant methods.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and antibodies. The terms "polypeptide", "protein," and "peptide" are used interchangeably herein. "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. "Domains" are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three dimensional structure of a polypeptide monomer. "Quaternary structure" refers to the three dimensional structure formed by the noncovalent association of independent tertiary units. A "motif" is a portion of a polypeptide sequence and includes at least two amino acids. A motif may be 2 to 20, 2 to 15, or 2 to 10 amino acids in length. In some embodiments, a motif includes 3, 4, 5, 6, or 7 sequential amino acids. A domain may be comprised of a series of the same type of motif.

"Recombinant" when used with reference, e.g., to a cell, or nucleic acid, protein, or vector, indicates that the cell, nucleic acid, protein, or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed, or not expressed at all.

"Sample" or "test sample" as used herein can mean any sample in which the presence and/or level of a target or activity is to be detected or determined or any sample comprising a compound as detailed herein. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pretreated, such as by filtration, distillation, extraction, concentration, centrifugation, inactivation of interfering components, addition of reagents, and the like, to modify the character of the sample in some manner as discussed herein or otherwise as is known in the art.

"Subject" and "patient" as used interchangeably herein can mean a mammal that wants or is in need of the herein described compounds. The subject may be a human or a non-human animal. The subject may be a vertebrate. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be male. The subject may be female. In some embodiments, the subject is human. In some embodiments, the subject has a specific genetic marker. The subject or patient may be undergoing other forms of treatment.

"Substantially identical" can mean that a first and second amino acid or polynucleotide sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 amino acids or nucleotides.

A "therapeutically effective amount" or "effective amount" as used interchangeably herein is an amount sufficient to elicit a therapeutic effect. Amounts effective for this use will depend on, e.g., the particular composition of the regimen administered, the manner of administration, the stage and severity of the disease, the general state of health of the subject, and the judgment of the prescribing physician. A therapeutically effective amount is also one in which any toxic or detrimental effects of substance are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

A therapeutically effective amount may be administered in one or more administrations (e.g., the composition may be given as a preventative treatment or therapeutically at any stage of disease progression, before or after symptoms, and the like), applications or dosages and is not intended to be limited to a particular composition, combination or administration route. It is within the scope of the present disclosure that the disclosed compositions may be administered at various times during the course of treatment of the subject. The times of administration and dosages used will depend on several factors, such as the goal of treatment (e.g., treating v. preventing), condition of the subject, etc. and can be readily determined by one skilled in the art. Administration may be adjusted according to individual need and professional judgment of a person administrating or supervising the administration of the compounds used in the present invention.

"Toxic" refers to a substance causing any adverse effect when administered to a subject. The term "non-toxic" refers to a substance that has a relatively low degree to which it can damage a subject. Toxicity can refer to the effect on a whole organism, such as an animal, bacterium, plant, or other subject as defined herein, as well as the effect on a substructure of the organism, such as a cell (cytotoxicity) or an organ (organotoxicity), such as the liver (hepatotoxicity). Toxicity may refer to hemolysis. Hemolysis refers to the rupture/lysis of red blood cells. The toxicity of GS is typically caused by hemolysis. A central concept of toxicology is that effects are dose-dependent; even water can lead to water intoxication when taken in large enough doses, whereas for even a very toxic substance such as snake venom there is a dose below which there is no detectable toxic effect. A composition or compound that is relatively non-toxic may allow a wider range of subjects to be able to safely handle the composition or compound, without serious safety concerns or risks.

"Treat," "treatment," or "treating," when referring to protection of a subject from a disease or infection means preventing, suppressing, repressing, ameliorating, or completely eliminating the pathological condition, disease, or infection. Preventing the pathological condition, disease, or infection involves administering a compound or composition of the present invention to a subject prior to onset of the pathological condition. Suppressing the pathological condition, disease, or infection involves administering a compound or composition of the present invention to a subject after induction of the pathological condition, disease, or infection but before its clinical appearance. Repressing or ameliorating the pathological condition, disease, or infection involves administering a compound or composition of the present invention to a subject after clinical appearance of the pathological condition, disease, or infection.

"Variant" as used herein with respect to a polynucleotide means (i) a portion or fragment of a referenced nucleotide sequence; (ii) the complement of a referenced nucleotide sequence or portion thereof; (iii) a polynucleotide that is substantially identical to a referenced polynucleotide or the complement thereof; or (iv) a polynucleotide that hybridizes under stringent conditions to the referenced polynucleotide, complement thereof, or a sequence substantially identical thereto.

A "variant" can further be defined as a peptide or polypeptide that differs in amino acid sequence by the insertion, deletion, or conservative substitution of amino acids, but retain at least one biological activity. Representative examples of "biological activity" include the ability to be bound by a specific antibody or polypeptide or to promote an immune response. Variant can mean a substantially identical sequence. Variant can mean a functional fragment thereof. Variant can also mean multiple copies of a polypeptide. The multiple copies can be in tandem or separated by a linker. Variant can also mean a polypeptide with an amino acid sequence that is substantially identical to a referenced polypeptide with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids. See Kyte et al., *J. Mol. Biol.* 1982, 157, 105-132. The hydropathic index of an amino acid is based on a consideration of its hydrophobicity and charge. It is known in the art that amino acids of similar hydropathic indexes can be substituted and still retain protein function. In one aspect, amino acids having hydropathic indices of ±2 are substituted. The hydrophobicity of amino acids can also be used to reveal substitutions that would result in polypeptides retaining biological function. A consideration of the hydrophilicity of amino acids in the context of a polypeptide permits calculation of the greatest local average hydrophilicity of that polypeptide, a useful measure that has been reported to correlate well with antigenicity and immunogenicity, as discussed in U.S. Pat. No. 4,554,101, which is fully incorporated herein by reference. Substitution of amino acids having similar hydrophilicity values can result in polypeptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant can be a polynucleotide sequence that is substantially identical over the full length of the full gene sequence or a fragment thereof. The polynucleotide sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant can be an amino acid sequence that is substantially identical over the full length of the amino acid sequence or fragment thereof. The amino acid sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl," as used herein, means a straight or branched, saturated hydrocarbon chain containing from 1 to 10 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, 4,4-dimethylpentan-2-yl, n-heptyl, n-octyl, n-nonyl, and n-decyl.

The term "alkenyl," as used herein, means a straight or branched, hydrocarbon chain containing at least one carbon-carbon double bond and from 1 to 10 carbon atoms.

The term "alkoxyalkyl," as used herein, refers to an alkoxy group, as defined herein, appended to the parent molecular moiety through an alkyl group, as defined herein.

The term "alkoxyfluoroalkyl," as used herein, refers to an alkoxy group, as defined herein, appended to the parent molecular moiety through a fluoroalkyl group, as defined herein.

The term "alkylene," as used herein, refers to a divalent group derived from a straight or branched chain hydrocarbon of 1 to 10 carbon atoms, for example, of 2 to 5 carbon atoms. Representative examples of alkylene include, but are not limited to, —$CH_2CH_2$—, —$CH_2CH_2CH_2$—, —$CH_2CH(CH_3)CH_2$—, —$CH_2CH_2CH_2CH_2$—, —$CH_2CH(CH_3)CH_2CH_2$—, and —$CH_2CH_2CH_2CH_2CH_2$—.

The term "alkylamino," as used herein, means at least one alkyl group, as defined herein, is appended to the parent molecular moiety through an amino group, as defined herein.

The term "amide," as used herein, means —C(O)NR— or —NRC(O)—, wherein R may be hydrogen, alkyl, cycloalkyl, aryl, heteroaryl, heterocycle, alkenyl, or heteroalkyl.

The term "aminoalkyl," as used herein, means at least one amino group, as defined herein, is appended to the parent molecular moiety through an alkylene group, as defined herein.

The term "amino," as used herein, means —$NR_xR_y$, wherein $R_x$ and $R_y$ may be hydrogen, alkyl, cycloalkyl, aryl, heteroaryl, heterocycle, alkenyl, or heteroalkyl. In the case of an aminoalkyl group or any other moiety where amino appends together two other moieties, amino may be —$NR_x$—, wherein $R_x$ may be hydrogen, alkyl, cycloalkyl, aryl, heteroaryl, heterocycle, alkenyl, or heteroalkyl.

The term "aryl," as used herein, refers to a phenyl group, or a bicyclic or tricyclic fused ring system. Bicyclic fused ring systems are exemplified by a phenyl group appended to the parent molecular moiety and fused to a phenyl group, a cycloalkyl group as defined herein, a heteroaryl group as defined herein, or a heterocycle as defined herein. Tricyclic fused ring systems are exemplified by a phenyl group appended to the parent molecular moiety and fused to a bicyclic fused ring system as described herein. Representative examples of aryl include, but are not limited to, phenyl, naphthyl, anthracenyl, indolyl (e.g., 1H-indol-4-yl, 1H-indol-6-yl, and 1H-indol-7-yl), benzodioxolyl (e.g., benzo[d][1,3]dioxol-4-yl and benzo[d][1,3]dioxol-5-yl), chromanyl (e.g., chroman-5-yl, chroman-6-yl, chroman-7-yl, and chroman-8-yl), and tetrahydroquinolinyl (e.g., 1,2,3,4-tetrahydroquinolin-5-yl, 1,2,3,4-tetrahydroquinolin-6-yl, 1,2,3,4-tetrahydroquinolin-7-yl, and 1,2,3,4-tetrahydroquinolin-8-yl).

The term "cyanoalkyl," as used herein, means at least one —CN group, is appended to the parent molecular moiety through an alkylene group, as defined herein.

The term "cyanofluoroalkyl," as used herein, means at least one —CN group, is appended to the parent molecular moiety through a fluoroalkyl group, as defined herein.

The term "cycloalkoxy," as used herein, refers to a cycloalkyl group, as defined herein, appended to the parent molecular moiety through an oxygen atom.

The term "cycloalkyl," as used herein, refers to a carbocyclic ring system containing three to ten carbon atoms, zero heteroatoms and zero double bonds. The cycloalkyl may be monocyclic, bicyclic, bridged, fused, or spirocyclic. Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, and bicyclo[1.1.1]pentanyl. "Cycloalkyl" also includes carbocyclic ring systems in which a cycloalkyl group is appended to the parent molecular moiety and is fused to an aryl group as defined herein (e.g., a phenyl group), a heteroaryl group as defined herein, or a heterocycle as defined herein. Representative examples of such cycloalkyl groups include, but are not limited to, 2,3-dihydro-1H-indenyl (e.g., 2,3-dihydro-1H-inden-1-yl and 2,3-dihydro-1H-inden-2-yl), 6,7-dihydro-5H-cyclopenta[b]pyridinyl (e.g., 6,7-dihydro-5H-cyclopenta[b]pyridin-6-yl), oxaspiro[3.3]heptanyl (e.g., 2-oxaspiro[3.3]heptan-6-yl), and 5,6,7,8-tetrahydroquinolinyl (e.g., 5,6,7,8-tetrahydroquinolin-5-yl).

The term "cycloalkenyl," as used herein, means a non-aromatic monocyclic or multicyclic ring system containing at least one carbon-carbon double bond and preferably having from 5-10 carbon atoms per ring. The cycloalkenyl may be monocyclic, bicyclic, bridged, fused, or spirocyclic. Exemplary monocyclic cycloalkenyl rings include cyclopentenyl, cyclohexenyl, cycloheptenyl, and bicyclo[2.2.1]heptenyl.

The term "fluoroalkyl," as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "fluoroalkoxy," as used herein, means at least one fluoroalkyl group, as defined herein, is appended to the parent molecular moiety through an oxygen atom. Representative examples of fluoroalkoxy include, but are not limited to, difluoromethoxy, trifluoromethoxy and 2,2,2-trifluoroethoxy.

The term "halogen" or "halo," as used herein, means Cl, Br, I, or F.

The term "haloalkyl," as used herein, means an alkyl group, as defined herein, in which one, two, three, four, five, six, seven or eight hydrogen atoms are replaced by a halogen.

The term "haloalkoxy," as used herein, means at least one haloalkyl group, as defined herein, is appended to the parent molecular moiety through an oxygen atom.

The term "halocycloalkyl," as used herein, means a cycloalkyl group, as defined herein, in which one or more hydrogen atoms are replaced by a halogen.

The term "heteroalkyl," as used herein, means an alkyl group, as defined herein, in which one or more of the carbon atoms has been replaced by a heteroatom selected from S, O, P and N. Representative examples of heteroalkyls include, but are not limited to, alkyl ethers, secondary and tertiary alkyl amines, amides, and alkyl sulfides.

The term "heteroaryl," as used herein, refers to an aromatic monocyclic ring or an aromatic bicyclic ring system. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, indolyl, pyridinyl (including pyridin-2-yl, pyridin-3-yl, pyridin-4-yl), pyrimidinyl, pyrazinyl, pyridazinyl, pyrazolyl, pyrrolyl, benzopyrazolyl, 1,2,3-triazolyl, 1,3,4-thiadiazolyl, 1,2,4-thiadiazolyl, 1,3,4-oxadiazolyl, 1,2,4-oxadiazolyl, imidazolyl, thiazolyl, isothiazolyl, thienyl, benzimidazolyl, benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl, quinazolinyl, 1,2,4-triazinyl, 1,3,5-triazinyl, isoquinolinyl, quinolinyl, 6,7-dihydro-1,3-benzothiazolyl, imidazo[1,2-a]pyridinyl, naphthyridinyl, pyridoimidazolyl, thiazolo[5,4-b]pyridin-2-yl, thiazolo[5,4-d]pyrimidin-2-yl.

The term "heterocycle" or "heterocyclic," as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, 2-oxo-3-piperidinyl, 2-oxoazepan-3-yl, oxadiazolinyl, oxadiazolidinyl, oxazolinyl, oxazolidinyl, oxetanyl, oxepanyl, oxocanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, 2-oxa-6-azaspiro[3.3]heptan-6-yl, azabicyclo[2.2.1]heptyl (including 2-azabicyclo[2.2.1]hept-2-yl), oxabicyclo[2.2.1]heptanyl (including 7-oxabicyclo[2.2.1]heptan-3-yl), azabicyclo[3.1.0]hexanyl (including 3-azabicyclo[3.1.0]hexan-3-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.13,7]decane), and oxa-adamantane (2-oxatricyclo[3.3.1.13,7]decane). The monocyclic, bicyclic, and tricyclic heterocycles are connected to the parent molecular moiety through any carbon atom or any nitrogen atom contained within the rings, and can be unsubstituted or substituted.

The term "hydroxyl" or "hydroxy," as used herein, means an —OH group.

The term "hydroxyalkyl," as used herein, means at least one —OH group, is appended to the parent molecular moiety through an alkylene group, as defined herein.

The term "hydroxyfluoroalkyl," as used herein, means at least one —OH group, is appended to the parent molecular moiety through a fluoroalkyl group, as defined herein.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

The term "sulfonamide," as used herein, means —S(O)$_2$NR$^d$— or —NR$^d$S(O)—, wherein R$^d$ may be hydrogen, alkyl, cycloalkyl, aryl, heteroaryl, heterocycle, alkenyl, or heteroalkyl.

The term "substituents" refers to a group "substituted" on an aryl, heteroaryl, phenyl or pyridinyl group at any atom of that group. Any atom can be substituted.

The term "substituted" refers to a group that may be further substituted with one or more non-hydrogen substituent groups. Substituent groups include, but are not limited to, halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl. For example, if a group is described as being "optionally substituted" (such as an alkyl, alkenyl, alkynyl, aryl, heteroaryl, cycloalkyl, heteroalkyl, heterocycle or other group such as an R group), it may have 0, 1, 2, 3, 4 or 5 substituents independently selected from halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkyl sulfonyl, aryl sulfonyl, aminosulfonyl, sulfinyl, —COOH, ketone, amide, carbamate, and acyl.

The term "---" designates a single bond (—) or a double bond (=).

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

When substituent groups are specified by their conventional chemical formulae, written from left to right, such a formula also encompasses the same substituent that would result from writing the structure from right to left. For example, —CH$_2$NH— is also intended to encompass —NHCH$_2$—.

2. COMPOUNDS

In one aspect, disclosed is a compound of formula (I),

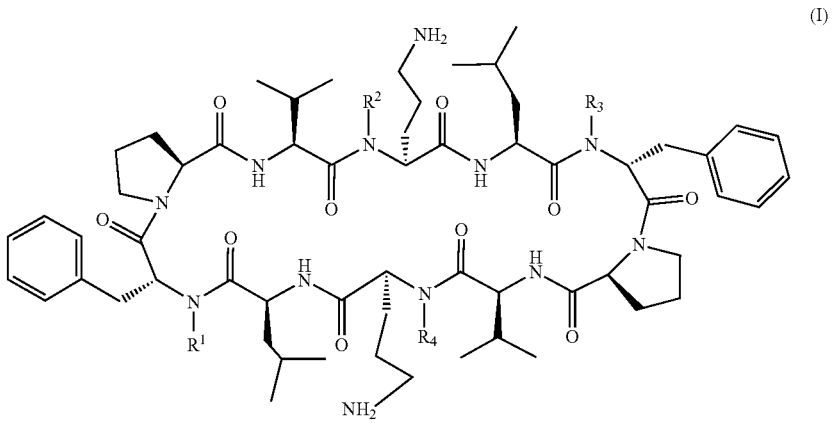

(I)

or a pharmaceutically acceptable salt thereof, wherein $R^1$, $R^2$, $R^3$, and $R^4$ are each independently selected from hydrogen or —NH$_2$.

At least one of $R^1$, $R^2$, $R^3$, and $R^4$ may be —NH$_2$. For example, $R^3$ may be —NH$_2$. As another example, $R^4$ may be —NH$_2$. At least two of $R^2$, $R^3$, and $R^4$ may be —NH$_2$. For example, $R^1$ and $R^3$ may be —NH$_2$. $R^3$ and $R^4$ may be —NH$_2$. $R^2$ and $R^3$ may be —NH$_2$. $R^2$ and $R^4$ may be —NH$_2$. At least three of $R^1$, $R^2$, $R^3$, and $R^4$ may —NH$_2$. For example, $R^1$, $R^3$, and $R^4$ may be —NH$_2$. $R^2$, $R^3$, and $R^4$ may be —NH$_2$. Each of $R^1$, $R^2$, $R^3$, and $R^4$ may be —NH$_2$.

Suitable compounds include:
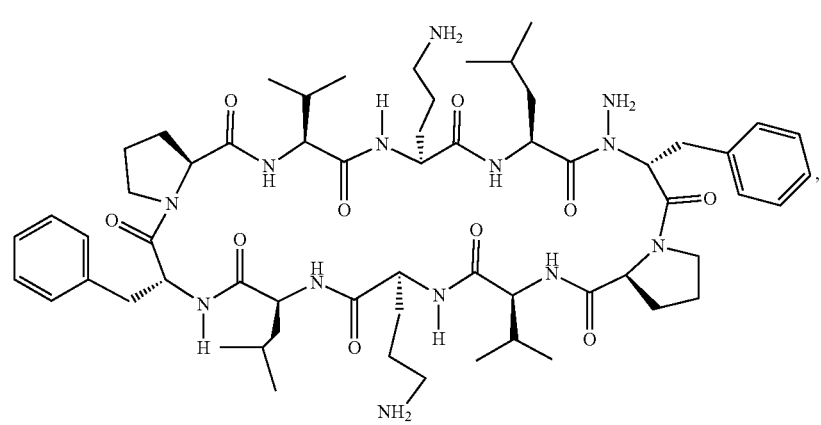
1
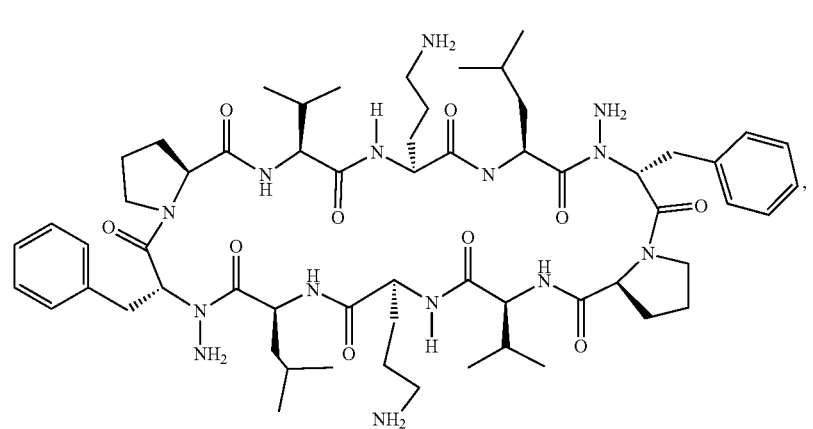
2
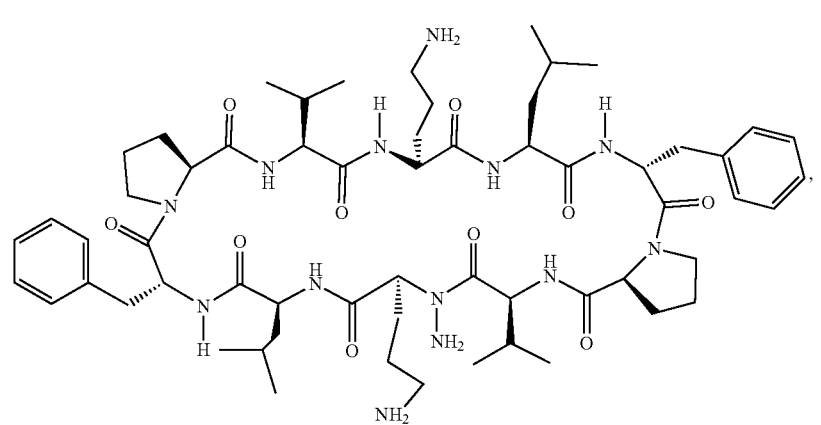
3

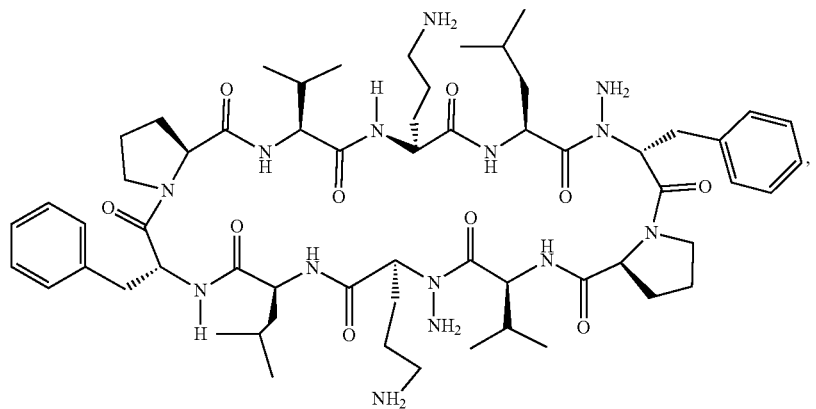
4
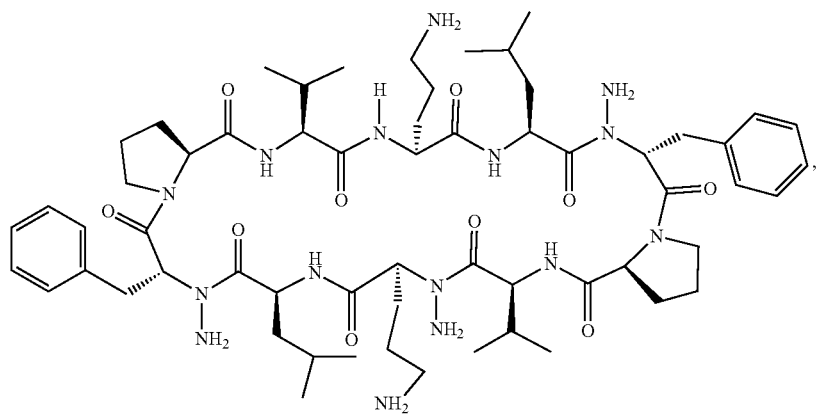
5
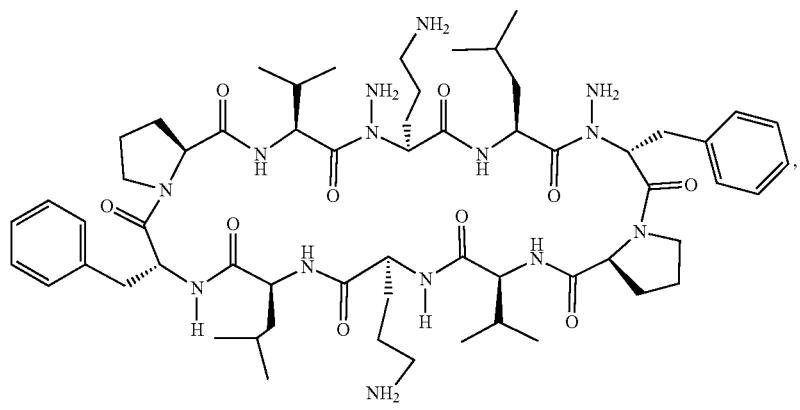
6
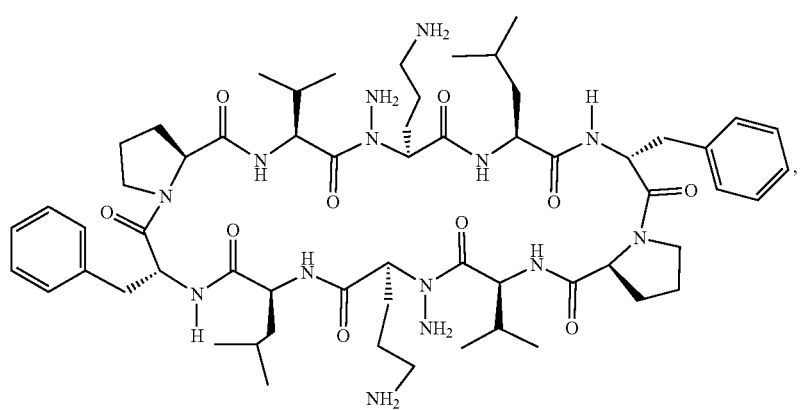
7

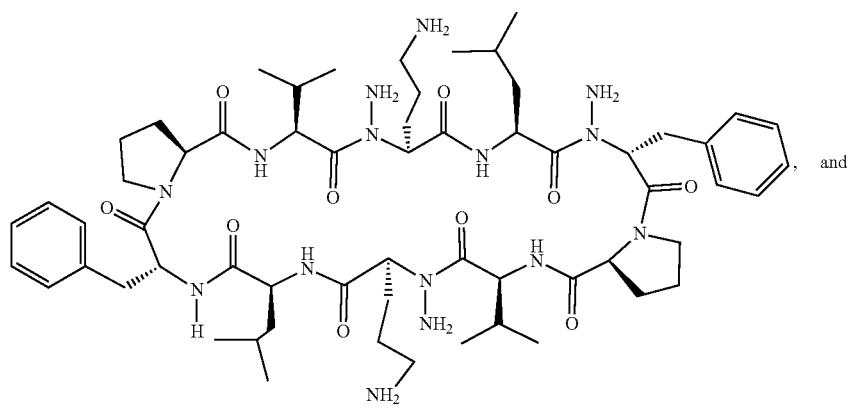

8

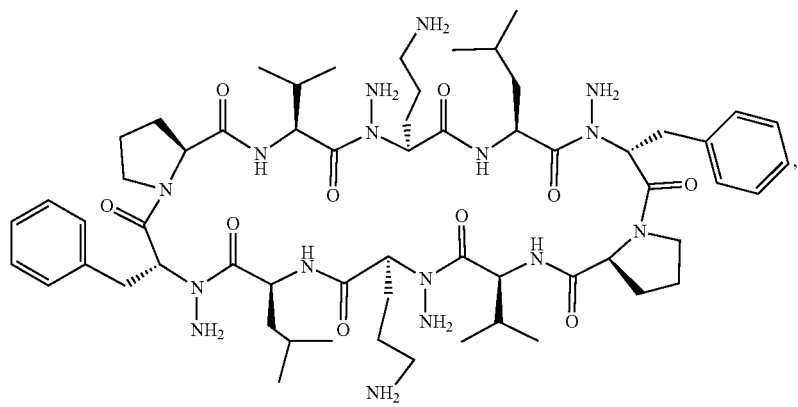

9 or a pharmaceutically acceptable salt thereof.

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry," 5th edition (1989), Longman Scientific & Technical, Essex CM20 2JE, England, or (2) direct separation of the mixture of optical enantiomers on chiral chromatographic columns, or (3) fractional recrystallization methods.

It should be understood that the compound may possess tautomeric forms, as well as geometric isomers, and that these also constitute embodiments of the disclosure.

The present disclosure also includes an isotopically-labeled compound, which is identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^{2}$H, $^{3}$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Substitution with heavier isotopes such as deuterium, i.e. $^{2}$H, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated are $^{11}$C, $^{13}$N, $^{15}$O, and $^{18}$F. Isotopically-labeled compounds can generally be prepared by conventional techniques known to those skilled in the art or by processes analogous to those described in the accompanying Examples using appropriate isotopically-labeled reagent in place of non-isotopically-labeled reagent.

a. Pharmaceutically Acceptable Salts

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

b. General Synthesis

N-amino peptides which retain their normal Cα substituents are constrained by both covalent and noncovalent interactions, which results in a reduction of the number of accessible torsion bond angles. In contrast to oligomeric N-alkylated peptides, the N-amino substituent in the N-amino peptides described herein offer additional sites for hydrogen bonding or subsequent chemical diversification.

Compounds of formula (I) may be synthesized through solution-phase or solid-phase peptide synthesis methods known in the art. Compounds of formula (I) may be synthesized by a process which includes (1) preparation of dipeptide building blocks for solid phase reaction, (2) loading amino acid and dipeptide building blocks onto a solid phase resin (such as 2-chlorotrityl chloride resin), (3) solid phase synthesis of a linear peptide, and (4) solution phase cyclization. In some embodiments, individual amino acid residues may be aminated, for example as aminated amino acid or aminated dipeptide, before they are used in solution-phase or solid-phase peptide synthesis to prepare the compounds of formula (I). A representative synthesis process is provided herein in the Examples. Representative compounds of formula (I) prepared by the synthesis process herein are shown in FIG. 1.

Reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the disclosure. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis (4th ed.), John Wiley & Sons, NY (2006), which is incorporated herein by reference in its entirety. Synthesis of the compounds of the disclosure can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the disclosure as it is defined in the appended claims. All alternatives, modifications, and equivalents of the synthetic methods and specific examples are included within the scope of the claims.

3. PHARMACEUTICAL COMPOSITIONS

The disclosed compounds may be incorporated into pharmaceutical compositions suitable for administration to a subject. The pharmaceutical composition may comprise the compound and a pharmaceutically acceptable carrier.

The pharmaceutical compositions may include a therapeutically effective amount of the compound. Any suitable therapeutically effective amount of the compound may be used in the pharmaceutical composition. For example, a therapeutically effective amount may be about 0.001 mg/kg to about 1000 g/kg, 0.01 mg/kg to about 100 g/kg, 0.1 mg/kg to about 10 g/kg, 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical composition may further comprise one or more pharmaceutically acceptable carriers. Pharmaceutically acceptable carriers typically include at least one of diluents, lubricants, binders, disintegrants, colorants, flavors, sweeteners, antioxidants, preservatives, glidants, solvents, suspending agents, wetting agents, surfactants, pH adjusting additives, combinations thereof, and others. The route by which the disclosed compounds are administered and the form of the composition will dictate the type of carrier to be used.

The pharmaceutical composition may be in a variety of forms, suitable for any desired mode of administration. For example, the composition may be in a form that is suitable for systemic administration (e.g., oral, rectal, sublingual, buccal, implants, intranasal, intravaginal, transdermal, intravenous, intraarterial, intratumoral, intraperitoneal, or parenteral) or topical administration (e.g., dermal, pulmonary, nasal, aural, ocular, liposome delivery systems, or iontophoresis). The compositions may conveniently be presented in unit dosage form and may be prepared by any methods well known in the art of pharmacy. Such methods include the step of bringing into association the active compound with the carrier which constitutes one or more accessory ingredients. In general, the compositions are prepared by uniformly and intimately bringing into association the active compound with liquid carriers or finely divided solid carriers or both, and then if necessary shaping the product. Compositions may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

Compositions suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Compositions suitable for topical administration (e.g. transdermal, intranasal, ocular, buccal, and sublingual) may be formulated as an ointment, cream, suspension, lotion, powder, solution, past, gel, spray, aerosol, or oil. Alternatively, a composition may comprise a patch or a dressing such as a bandage or adhesive plaster impregnated with active compounds and optionally one or more excipients or diluents.

Compositions suitable for topical administration in the mouth include lozenges comprising the active compound in a flavored basis, usually sucrose and acacia or tragacanth; pastilles comprising the active compound in an inert basis such as gelatin and glycerin, or sucrose and acacia; and mouthwashes comprising the active compound in a suitable liquid carrier.

Compositions suitable for topical administration to the eye also include eye drops wherein the active compound is dissolved or suspended in a suitable carrier, especially an aqueous solvent for the active compound.

Compositions suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable compositions wherein the carrier is a liquid for administration as, for example, nasal spray, nasal drops, or by aerosol administration by nebulizer, include aqueous or oily solutions of the active compound.

Compositions suitable for administration by inhalation include those presented as an aerosol spray from a pressurized pack, with the use of a suitable propellant, such as dichlorodifluoromethane, trichlorofluoromethane, dichorotetrafluoroethane, carbon dioxide, or other suitable gases.

Compositions suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical compositions may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream compositions.

Suitable emulgents and emulsion stabilizers include Tween 60, Span 80, cetostearyl alcohol, myristyl alcohol, glyceryl monostearate and sodium lauryl sulphate. The choice of suitable oils or fats for the composition is based on achieving the desired cosmetic properties, since the solubility of the active compound in most oils likely to be used in pharmaceutical emulsion compositions may be very low. Thus the cream should preferably be a non-greasy, non-staining and washable product with suitable consistency to avoid leakage from tubes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Compositions suitable for rectal administration may be presented as a suppository with a suitable base comprising, for example, cocoa butter or a salicylate.

Compositions suitable for vaginal administration may be presented as pessaries, tampons, creams, gels, pastes, foams or spray compositions containing in addition to the active compound, such carriers as are known in the art to be appropriate.

The term parenteral as used herein includes subcutaneous, intravenous, intramuscular, intrathecal, or intrasternal injection, or infusion techniques. Injectable preparations, for example, sterile injectable aqueous or oleaginous suspensions, may be formulated according to the known art using suitable pharmaceutically acceptable carriers. The sterile injectable preparation may also be a sterile injectable solution or suspension in a nontoxic pharmaceutically acceptable carrier. Among the acceptable carriers that may be employed are water, Ringer's solution, isotonic sodium chloride solution. In addition, sterile, fixed oils may be used as a carrier. For this purpose, any bland fixed oil may be employed, including synthetic mono- or diglycerides. In addition, fatty acids such as oleic acid may be used. Other suitable pharmaceutically acceptable carriers include dimethyl acetamide, surfactants including ionic and non-ionic detergents, and polyethylene glycols. The disclosed compositions may be sterile and stable under the conditions of manufacture and storage. For this purpose, suitable preservatives may be used in the disclosed compositions. For example, the disclosed compositions may comprise benzalkonium chloride, methyl paraben and/or sodium benzoate. The amount of preservative(s) in a composition is typically about 0.01 to about 5%. Suitable pH adjusting additives may also be added to the pharmaceutical composition. Suitable pH adjusting additives include HCl or NaOH in amounts sufficient to adjust the pH of the pharmaceutical composition. Mixtures of pharmaceutically acceptable carriers such as those discussed above may also be used.

4. METHODS OF TREATING INFECTION

The disclosure provides a method for treating an infection in a subject. The method may comprise administering the disclosed compounds or compositions to a subject. The subject may be diagnosed with or at risk of developing an infection. The infection may be a multi-drug resistant infection.

The infection may be a fungal infection. For example, the infection may be a fungal infection on the skin. The fungal infection on the skin may infect any part of the body, for example the legs, arms, stomach, or scalp. The fungal infection may be on the fingernails or toenails. The fungal infection may be inside the body. For example, the fungal infection may be in the lungs or in the vagina. The subject may be infected with any fungus, including but not limited to *Aspergillus, Candida, Coccidioides, Cryptococcus gatti, Pneumocystis jirovecii, Blastomyces, Cryptoccocus neoformans, Histoplasma,* or *Talaromyces.* The fungal infection may lead to a pathological condition in the subject. For example, the fungal infection may lead to aspergillosis, candidiasis, coccidioidomycosis, fungal nail infections, mucormycosis, *Pneumocystis* pneumonia, sporotrichosis, blastomycosis, candida auris, C. neuroforms infection, meningitis, fungal eye infections, histoplasmosis, mycetoma, ringworm, talaromycosis, and the like. The disclosed compounds or compositions may be administered to a subject in an effective amount to treat the pathological condition in the subject.

The infection may be a bacterial infection. The bacterial be a gram-positive bacterial infection. Gram-positive bacteria include, for example, *Actinomyces* spp. (*A. israelii*); *Aerococcus* spp.; *Bacillus* spp. (*B. anthracis*); *Bacterionema* spp.; *Bifidobacterium* spp.; *Clostridium* spp. (*C. botulinum, C. difficile, C. perfringens, C. tetani*); *Corynebacterium* spp. (*C. diphtherias*); *Corprococcus* spp.; *Deinobacter* spp.; *Deinococcus* spp.; *Enterococcus* spp. (*E. faecalis, E. faecium*); *Erysipelothrix* spp.; *Eubacterium* spp.; *Gemella* spp.; *Lactobacillus* spp.; *Lactococcus* spp.; *Leuconostoc* spp.; *Listeria* spp. (*L. monocytogenes*); *Marinococcus* spp.; *Melissococcus* spp.; *Methanobacterium* spp.; *Micrococcus* spp.; *Mycobacterium* spp. (*M. avium, M. leprae, M. lepromatosis, M. tuberculosis, M. ulcerans*); *Micropolyspora* spp.; *Nocardia* spp. (*N. asteroides*); *Pediococcus* spp.; *Peptococcus* spp.; *Peptostreptococcus* spp.; *Planococcus* spp.; *Propionibacterium* spp.; *Rothia* spp.; *Ruminococcus* spp.; *Saccharococcus* spp.; *Salinococcus* spp.; *Carcina* spp.; *Staphylococcus* spp. (*S. aureus, S. epidermidis, S. saprophyticus*); *Stomatococcus* spp.; *Streptococcus* spp. (*S. agalactiae, S. pneumoniae, S. pyogenes, S. viridans*); *Streptomyces* spp.; *Trichococcus* spp.; and *Vagococcus* spp. The subject may be infected with or at risk of infection from any combination of gram-positive bacteria.

The infection may be a gram-negative bacterial infection. Gram-negative bacteria include, for example, *Acinetobacter* spp. (*A. baumannii*); *Bacterioides* spp. (*B. fragilis*); *Bordetella* spp. (*B. pertussis*); *Borrelia* spp. (*B. burgdorferi, B. garinii, B. afzelii*); *Brucella* spp. (*B. abortus, B. canis, B. melitensis, B. suis*); *Burkholderia* spp. (*B. mallei, B. pseudomallei*); *Calymmatobacterium* spp.; *Campylobacter* spp. (*C. fetus, C. jejuni*); *Chlamydia* spp. (*C. trachomatis, C. pneumoniae, C. psittaci*); *Chlamydophila* spp. (*C. pneumoniae*); *Citrobacter* spp.; *Coxiella* spp. (*C. burnetti*); *Edwardsiella* spp.; *Enterobacter* spp.; *Ehrlichia* spp. (*E. canis, E. chaffeensis*); *Escherichia* spp. (*E. coli*); *Francisella* spp. (*F. tularensis*); *Gardnerella* spp.; *Haemophilus* spp. *H. influenzae*); *Helicobacter* spp. *H. pylori*); *Klebsiella* spp. (*K. pneumoniae*); *Legionella* spp. (*L. pneumophila*); *Leptospira* spp. (*L. interrogans*); *Moraxella* spp. (*M. catarrhalis*); *Mycoplasma* spp. (*M. pneumoniae*); *Neisseria* spp. (*N. gonorrhoeae, N. meningitidis*); *Pasteurella* spp.; *Proteus* spp.; *Providencia* app.; *Pseudomonas* spp. (*P. aeruginosa, P.*

*mallei*); *Rickettsia* spp. (*R. akari, R. prowazekii, R. rickettsia*); *Salmonella* spp. (*S. enterica, S. enterica enteritidis, S. enterica* hadar, *S. enterica* Heidelberg, *S. enterica infantis, S. enterica* paratyphi, *S. enterica typhi, S. enterica typhimurium*); *Serratia* spp.; *Shigella* spp. (*S. dysenteriae, S. sonnei*); *Spirillaceae* spp. (*S. minus*); *Streptobacillus* spp. (*S. moniliformis*); *Treponema* spp. (*T. pallidum*); *Vibrio* spp. (*V. cholerae*); and *Yersinia* spp. (*Y. enterocolitica, Y. pestis, Y. pseudotuberculosis*). The subject may be infected with or at risk of infection from any combination of gram-negative bacteria. The subject may be infected with or at risk of infection from both gram-positive and gram-negative bacteria.

The bacterial infection may lead to a pathological condition in the infected subject. The disclosed compounds or compositions may be administered to a subject in an effective amount to treat the pathological condition. The pathological condition may be caused by a gram-positive bacteria. Pathological conditions in humans caused by Gram-positive bacteria include, for example, local and systemic staphylococcal infections, toxic shock syndrome (caused by, for example, Staphylococcal), sepsis (caused by, for example, *Streptococcus, Staphylococcus*), erysipelas (caused by, for example, *Streptococcus*), scarlet fever (caused by, for example, *Streptococcus*), botulism (caused by, for example, *C. botulinum*), tetanus (caused by, for example, *C. tetani*), leprosy (caused by, for example, *M. leprae, M. lepromatosis*), impetigo (caused by, for example, *S. aureus, S. pyogenes*), actinomycosis (caused by, for example, *A. israelii*), anthrax (caused by, for example, *B. anthracis*), Buruli ulcer (caused by, for example, *M. ulcerans*), tuberculosis (cause by, for example, *M. tuberculosis*), and cellulitis (caused by, for example, *Streptococcus*).

The pathological condition may be caused by a gram-negative bacteria. Pathological conditions in humans caused by Gram-negative bacteria include, for example, pneumonia such as pneumococcal pneumonia, sepsis (caused by, for example, *N. meningitides, K. pneumoniae*), typhoid fever (caused by, for example, *Salmonella*), diphtheria (caused by, for example, *C. diphtherias*), syphilis (caused by, for example, *T. palladium*), Q fever (caused by, for example, *C. burnetii*), Black Plague (caused by, for example, *Y. pestis*), Bubonic Plague (caused by, for example, *Y. pestis*), Pneumonic Plague (caused by, for example, *Y. pestis*), chlamydia (caused by, for example, *C. trachomatis*), gonorrhea (caused by, for example, *N. gonorrhoeae*), whooping cough (caused by, for example, *B. pertussis*), lyme disease (caused by, for example, *B. burgdorferi*), bacterial meningitis (caused by, for example, *H. influenzae*), Legionnaire's Disease (caused by, for example, *L. pneumophila*), Rocky Mountain Spotted Fever (caused by, for example, *R. rickettsia*), glanders (caused by, for example, *B. mallei*), and cholera (caused by, for example, *V. cholerae*).

Pathological conditions in humans caused by bacteria may further include, for example, osteomyelitis, pyoderma, bacterial vaginosis, urinary tract infection, brucellosis, dysentery, and bacterial gastroenteritis.

The disclosed compounds or compositions may be administered to the subject by any suitable route. For example, the disclosed compounds or compositions may be administered orally, parentally, by infusion, or co-administered as a component of any medical device or object to be inserted (temporarily or permanently) into a subject. Administration methods may be effective to circumvent the blood-brain barrier and are effective to deliver the disclosed compounds or compositions to the central nervous system. For example, delivery methods may include the use of nanoparticles. The particles may be of any suitable structure. Positively charged lipids are particularly preferred for the composition of such nanoparticles.

The amount of the compounds or compositions to be administered may depend on a variety of factors and may vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

In general, suitable dosage ranges of the disclosed compounds or compositions include from about 0.001 mg compound/kg body weight to about 1000 g/kg, 0.01 mg/kg to about 100 g/kg, 0.1 mg/kg to about 10 g/kg, 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

Administration can occur in one dose, continuously or intermittently (e.g., in divided doses at appropriate intervals) throughout the course of treatment. Methods of determining the most effective means and dosage of administration are well known to those of skill in the art and will vary with the composition used for therapy, the purpose of the therapy, the target cell being treated, and the subject being treated. Single or multiple administrations can be carried out with the dose level and pattern being selected by the treating physician.

The disclosed compounds or compositions may be administered to the patient at any frequency necessary to achieve the desired therapeutic effect. The compound or composition may be administered once, on a continuous basis (e.g. by an intravenous drip), or on a periodic/intermittent basis. Administration of the compounds or compositions may be repeated until the desired therapeutic effect has been achieved. For example, the compounds or compositions may be administered once to several times every month, every two weeks, every week, or every day. Administration of the compounds or compositions may be repeated until the desired therapeutic effect has been achieved. For example, the compounds or compositions may be administered once to several times over the course of 1 day, 3 days, 5 days, 1 week, 2 weeks, 3 weeks, 1 month, 2 months, 3 months, 4 months, 5 months, 6 months, 7 months, 8 months, 9 months, 10 months, 11 months, 12 months, or more. The compound or composition may be administered as part of a therapeutic regimen along with other treatments appropriate for the particular injury or disease being treated. For example, the compound may be administered along with other suitable antimicrobial agents.

5. EXAMPLES

The disclosed compounds, compositions, processes, and methods will be better understood by reference to the following examples, which are intended as an illustration of and not a limitation upon the scope of the invention. Where the term comprising is used herein, it should be understood that the disclosure also contemplates alternative embodiments consisting of or consisting essentially of the recited features.

Example 1

Exemplary Synthesis of N-Aminated Gramicidin S Analogues

Dipeptides for solid phase reactions were prepared according to Scheme 1.

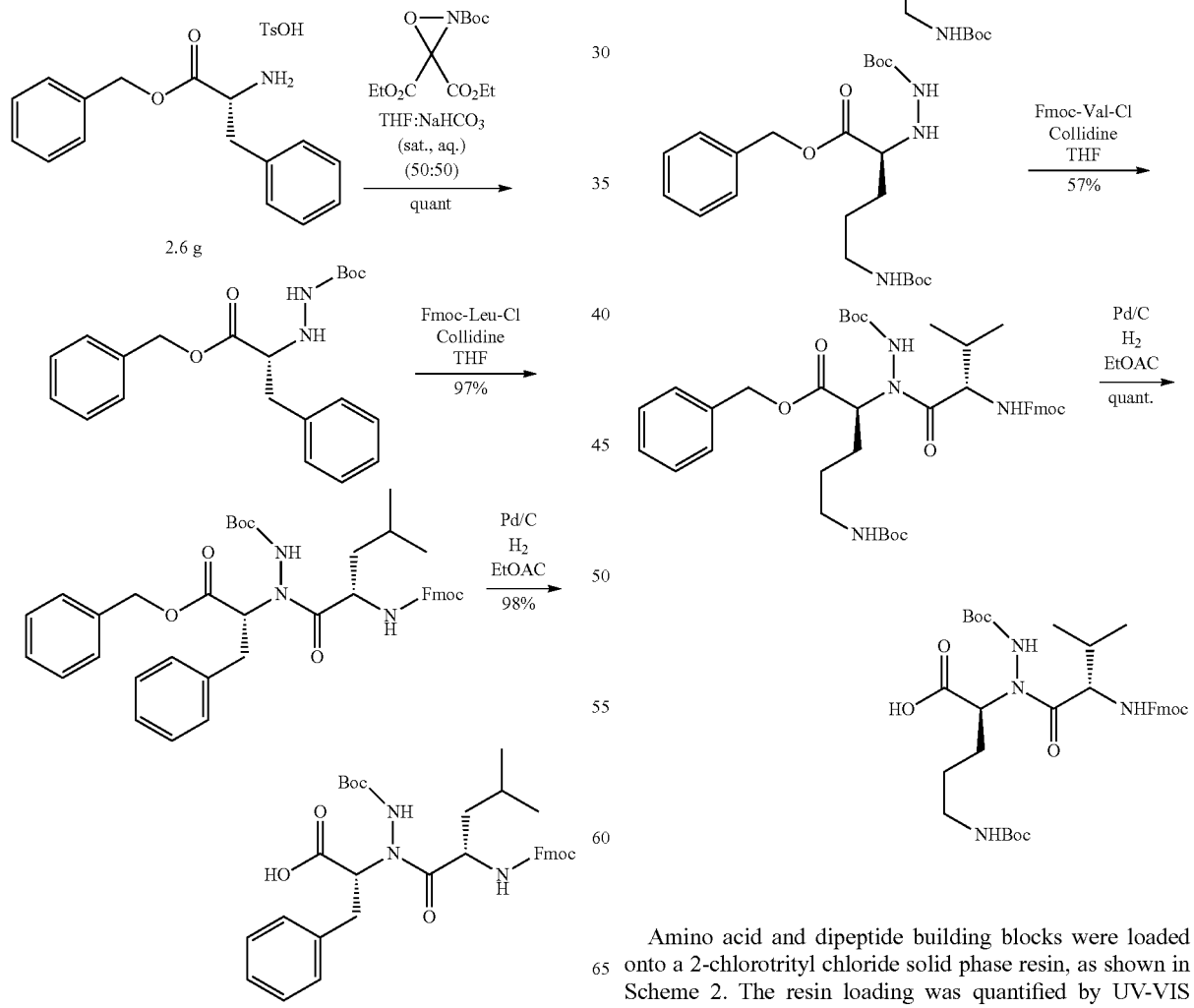

Figure 2:
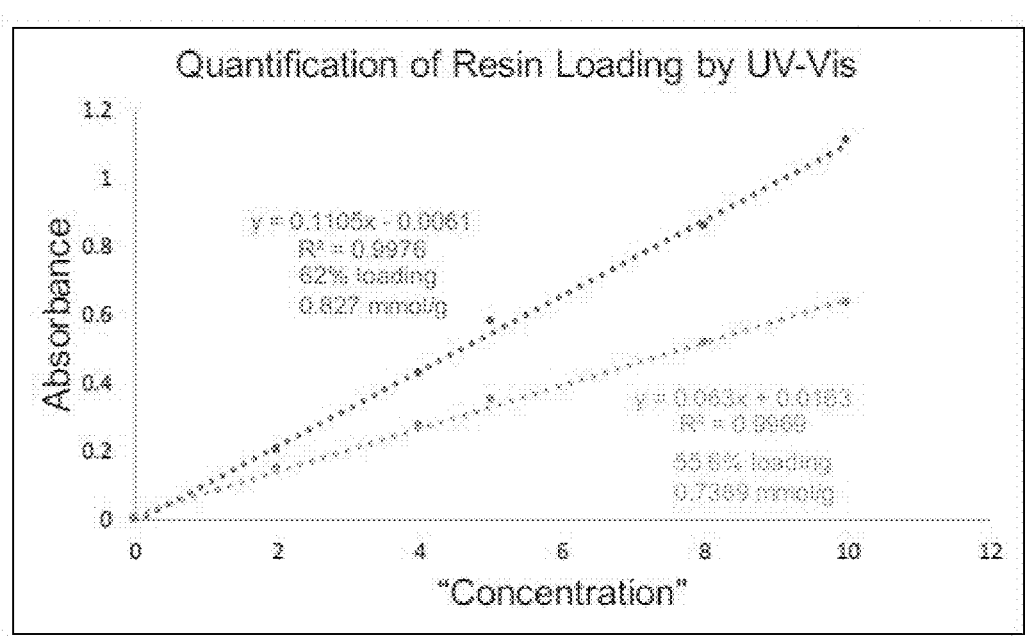
FIG. 2 shows representative UV-VIS spectra for quantification of resin loading.

Amino acid and dipeptide building blocks were loaded onto a 2-chlorotrityl chloride solid phase resin, as shown in Scheme 2. The resin loading was quantified by UV-VIS (FIG. 2).

Scheme 2 Loading the 2-Chlorotrityl Chloride Resin
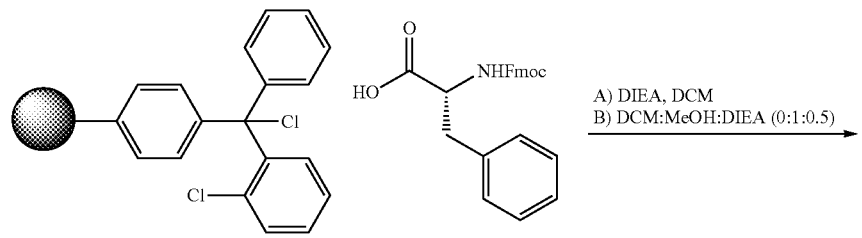
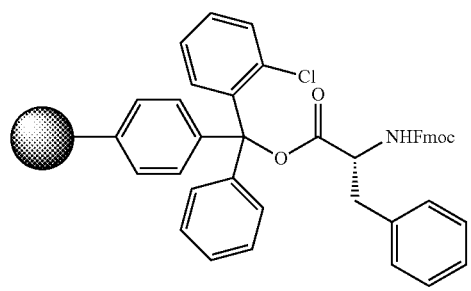
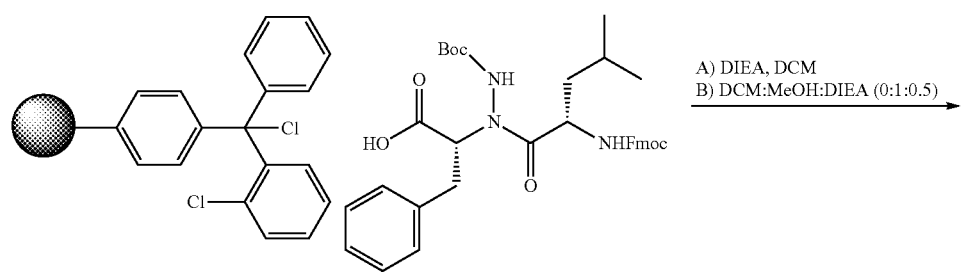
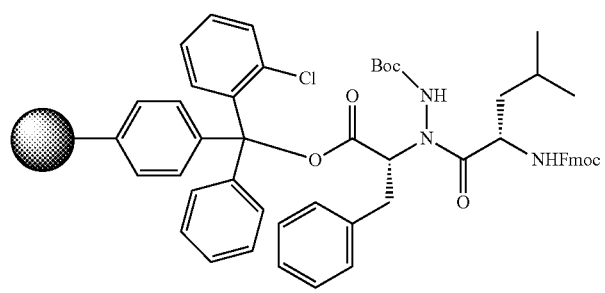
Linear peptides were synthesized according to Scheme 3.
Scheme 3 Solid-Phase Synthesis of the Linear Peptides
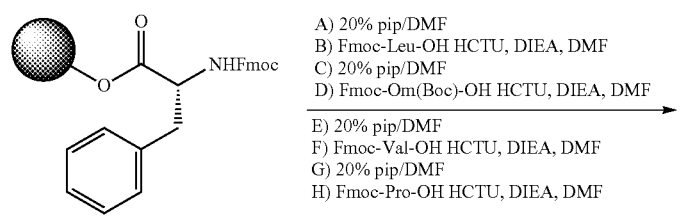
A) 20% pip/DMF
B) Fmoc-Leu-OH HCTU, DIEA, DMF
C) 20% pip/DMF
D) Fmoc-Orn(Boc)-OH HCTU, DIEA, DMF
E) 20% pip/DMF
F) Fmoc-Val-OH HCTU, DIEA, DMF
G) 20% pip/DMF
H) Fmoc-Pro-OH HCTU, DIEA, DMF

33

-continued

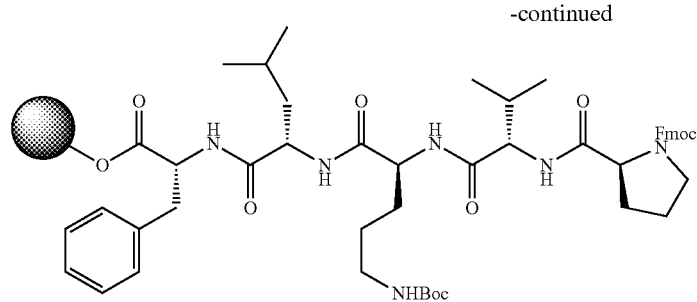

I) 20% pip/DMF
J) Fmoc-D-Phe-OH HCTU, DIEA, DMF
K) 20% pip/DMF
L) Fmoc-Leu-OH HCTU, DIEA, DMF
M) 20% pip/DMF
N) Fmoc-Orn(Boc)-OH HCTU, DIEA, DMF O) 20% pip/DMF
P) Fmoc-Val-OH HCTU, DIEA, DMF
Q) 20% pip/DMF
R) Fmoc-Pro-OH HCTU, DIEA, DMF
S) 20% pip/DMF
T) 20% HFIP/DCM

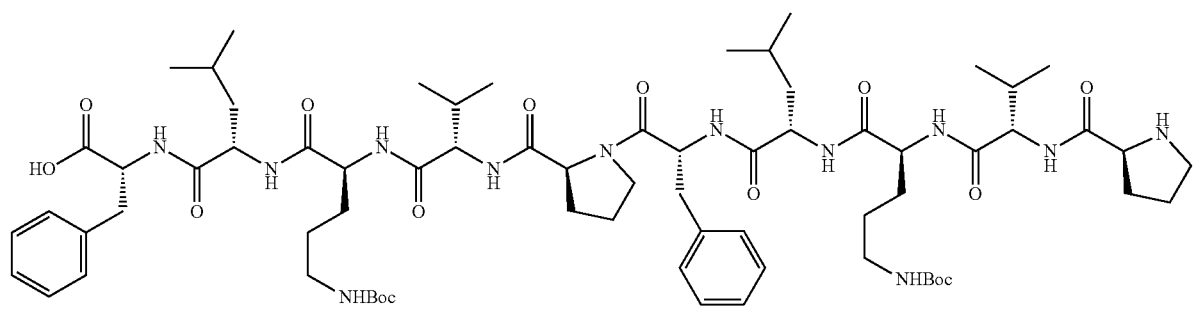

30

GS and GS analogs (FIG. 1) were prepared by solution phase cyclization according to Scheme 4.

Scheme 4 Representative Solution-Phase Cyclization

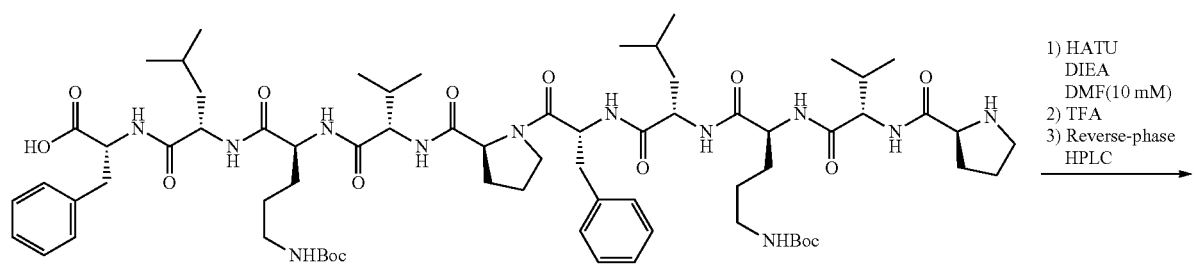

1) HATU
   DIEA
   DMF(10 mM)
2) TFA
3) Reverse-phase HPLC

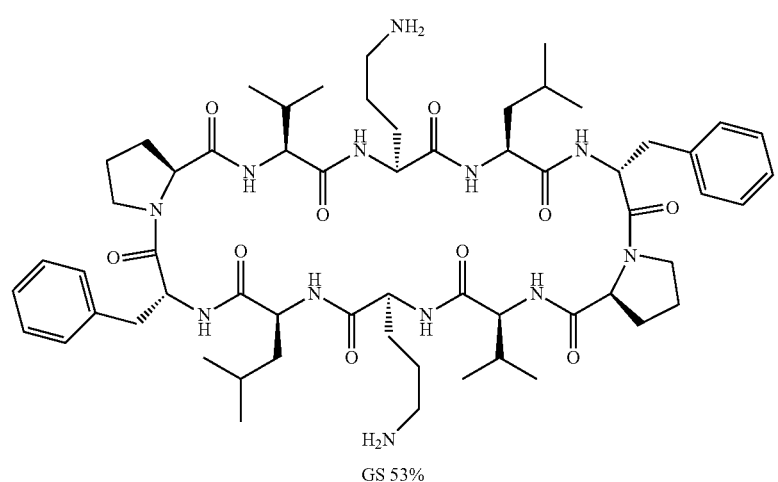

GS 53%

Figure 3A:
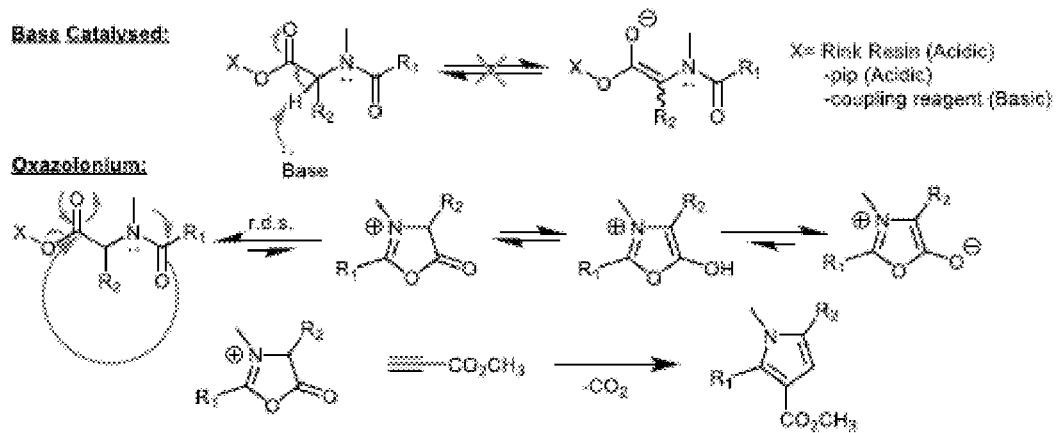
FIG. 3A shows a potential mechanism for epimerization during coupling reaction.
Figure 3B:
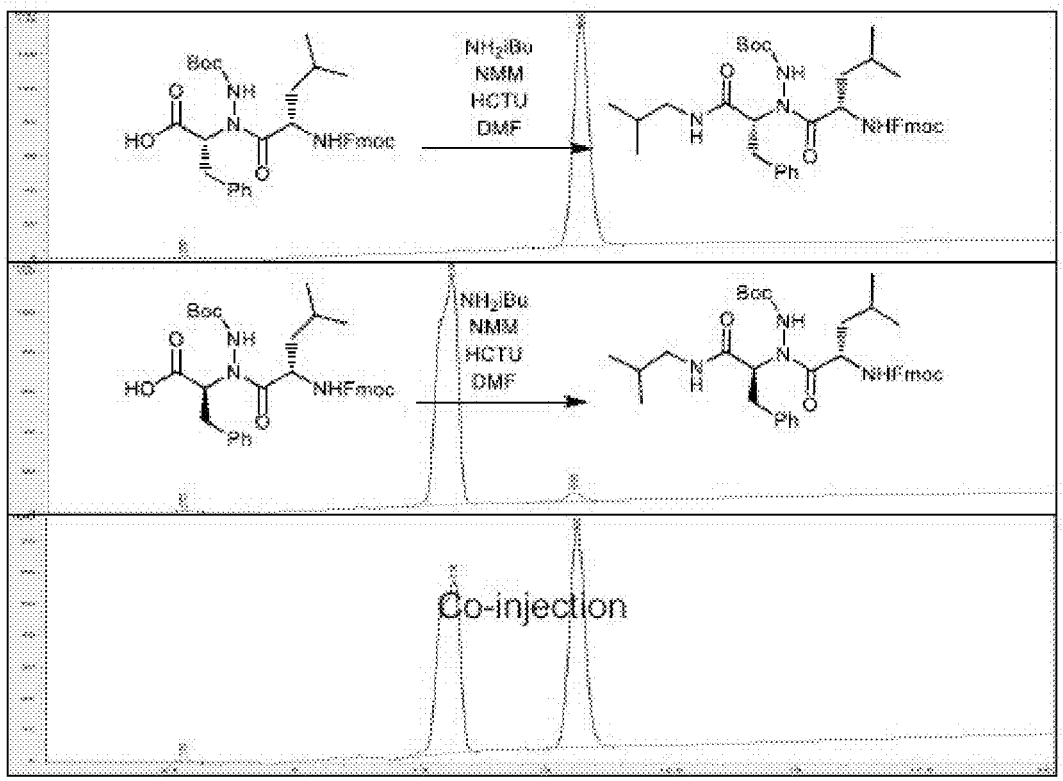
FIG. 3B shows that N-aminated representative coupling.
Figure 3C:
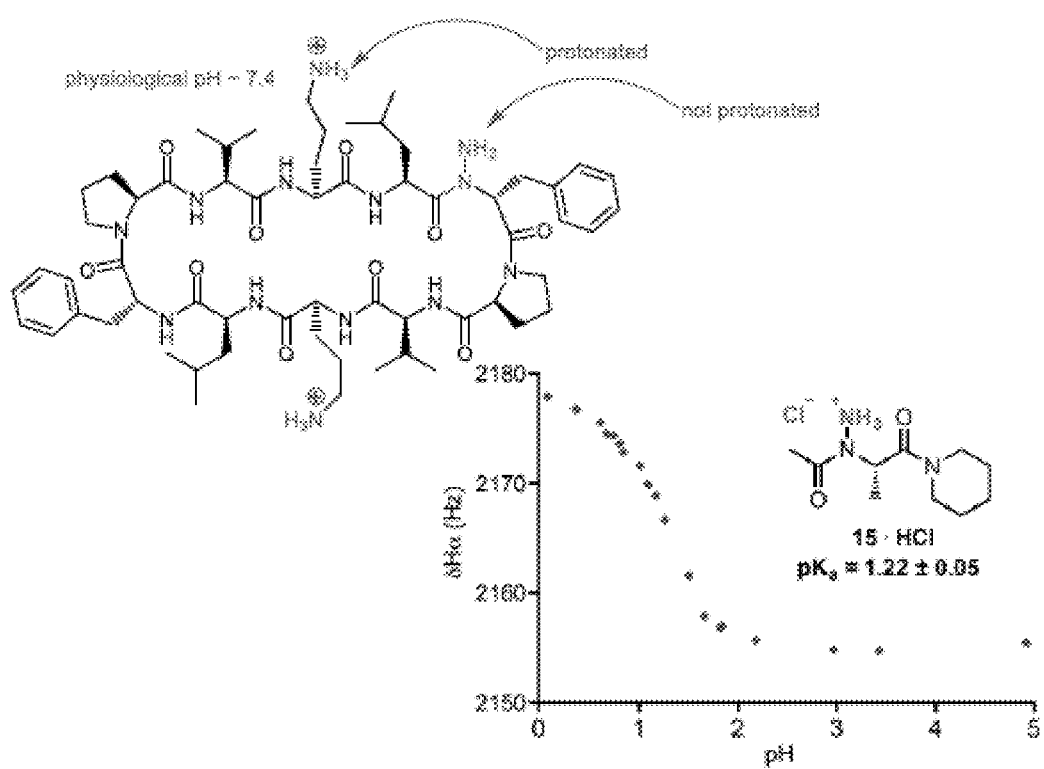
FIG. 3C shows that the N-amino compound is neutral at physiological pH.

It was hypothesized that epimerization could occur during coupling, for example, by the mechanisms illustrated in FIG. 3A. However, it was observed that N-aminated dipeptides do not epimerize (FIG. 3B). In addition, the N-amino compound is neutral at physiological pH (FIG. 3C).

Example 2

Activity of N-Aminated GS Analogues

Antimicrobial Activity:

The antimicrobial activity of the compounds disclosed herein was tested against a variety of bacteria. Bacterial strains tested are shown in Table 1. The bacterial strains comprised a panel of drug-resistant gram-positive and gram-negative bacteria known as ESKAPE pathogens. The minimum inhibitory concentration (MIC) for the compounds were determined as follows. Broth cultures of ESKAPE strains were grown overnight before being diluted 1 in 1000 in fresh media. Sterile 96-well plates were loaded with culture, and compounds (in DMSO) were added at decreasing concentrations to equal a total volume of 200 µL per well. Care was taken to not add more than 2.0% DMSO to any well. Plates were then incubated at 37° C., and MICs determined after 24 h by visual inspection for a lack of turbidity in wells. All assays were performed in triplicate with identical results obtained. The antimicrobial activities of the representative compounds are shown in Table 2. $MIC_{90}$ shows the minimum inhibitory concentration (µM) that inhibits 90% of bacterial isolates after 20 h, relative to a control culture.

TABLE 2

| | $MC_{90}$ Results (µM) | | | | | |
|---|---|---|---|---|---|---|
| GS | Ef (+) 3 | Sa (+) 3 | Kp (−) 40 | Ab (−) 6.5 | Pa (−) 20 | Ec (−) 35 |
| 1 | >50 | >50 | >50 | >50 | >50 | >50 |
| 2 | 4 | 4 | >50 | 12.5 | 35 | >50 |
| 3 | 3 | 2 | 40 | 6.5 | 13 | 30 |
| 4 | 3 | 2 | 45 | 6.5 | 15 | 30 |
| 5 | 3 | 3 | 50 | 6.5 | 20 | 35 |
| 6 | 3 | 2 | 45 | 6.5 | 15 | 15 |
| 7 | 2 | 2 | 45 | 4 | 10 | 20 |
| 8 | 2 | 2 | >50 | 6 | 12 | >50 |
| 9 | 2 | 2 | >50 | 5 | 15 | >50 |

Figure 4:
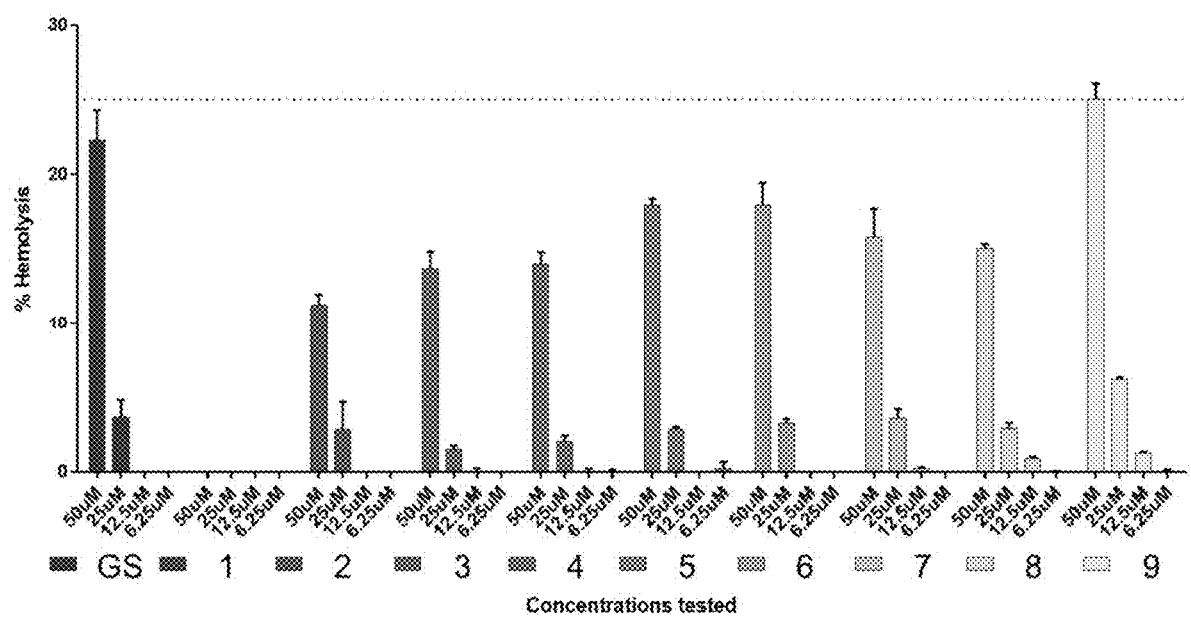
FIG. 4 shows the hemolytic activity of representative compounds of formula (I) at various concentrations.

Hemolytic Activity: The hemolytic activity of the compounds disclosed herein was also tested. A hemolysis assay was performed using whole human blood (Bioreclamation). Human red blood cells (hRBCs) were resuspended 20% v/v in 1×HA buffer (4.25 mL 10% NaCl; 1 mL CaCl2 in 50 mL sterile water), and compounds were added at a concentration of 10 µM to a final volume of 100 µL. Cells were incubated for 15 min at 37° C. before being centrifuged at 5500 g for 1 min to pellet nonlysed hRBCs. The supernatant was removed, added to a 96-well microtiter plate, and the $OD_{543}$ was read using a Biotek synergy2 plate reader. The negative control was vehicle only (DMSO), and the positive control was 1.0% triton X-100. Assays were performed in triplicate, with data displayed as percent hemolysis compared to controls, defined as percent hemolysis=($OD_{543}$ test sample−$OD_{543}$ no drug control)/($OD_{543}$ triton X-100−$OD_{543}$ no drug control)×100. Representative hemolytic activity (% hemolysis) is shown in Table 3. Representative results comparing GS and the compounds disclosed herein are shown in FIG. 4.

TABLE 3

| Hemolytic Activity (% Hemolysis) | | | | | | | | | |
|---|---|---|---|---|---|---|---|---|---|
| [ ] | GS | 1 | 2 | 3 | 4 | 5 | 6 | 7 | 8 | 9 |
| 50 µM | 22.30 | 0.00 | 11.24 | 13.68 | 14.00 | 17.93 | 17.91 | 15.84 | 15.07 | 25.01 |
| 25 µM | 3.65 | 0.00 | 2.84 | 1.49 | 1.98 | 2.82 | 3.24 | 3.57 | 2.91 | 6.19 |
| 12.5 µM | 0.00 | 0.00 | 0.00 | 0.00 | 0.00 | 0.00 | 0.00 | 0.21 | 0.88 | 2.75 |
| 6.25 µM | 0.00 | 0.00 | 0.00 | 0.00 | 0.00 | 0.21 | 0.00 | 0.00 | 0.00 | 0.00 |

TABLE 1

| Species | Strain # |
|---|---|
| Enterococcus faecium | 1450 |
| Staphylococcus aureus | 635 |
| Klebsiella penumoniae | 1433 |
| Acinetobacter baumannii | 5075 |
| Pseudomonas aeruginosa | 1419 |
| Enterobacter cloacae | 1454 |

These results show that the synthetic analogs herein have improved therapeutic properties compared to GS. Thus, an efficient protocol for the synthesis of N-aminated analogous of GS was developed. Against gram-positive bacteria GS analogues retained their activity while the activity against gram-negative bacteria improved significantly, especially for compounds 6 and 7. All the analogues tested showed reduced toxicity to human cells compared to GS with the exception of compound 9. Without being limited to any particular theory, it is hypothesized that the improved therapeutic profile of these analogues (as compared to GS) may be due to the enhanced stability of the β-sheet like character that the conformational constraints of N-amination afford to the peptides.

For reasons of completeness, various aspects of the invention are set out in the following numbered clauses:

Clause 1: A compound of formula (I),

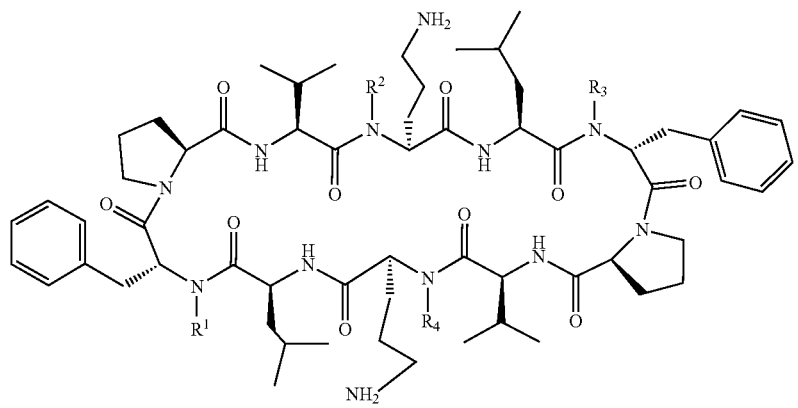

(I)

or a pharmaceutically acceptable salt thereof, wherein $R^1$, $R^2$, $R^3$, and $R^4$ are each independently selected from hydrogen or —$NH_2$.

Clause 2: The compound of clause 1, wherein at least one of $R^1$, $R^2$, $R^3$, and $R^4$ is —$NH_2$.

Clause 3: The compound of clause 2, wherein R3 is —$NH_2$.

Clause 4: The compound of claim 2, wherein R4 is —$NH_2$.

Clause 5: The compound of clause 1, wherein two of $R^1$, $R^2$, $R^3$, and $R^4$ are —$NH_2$.

Clause 6: The compound of clause 5, wherein $R^1$ and $R^3$ are —$NH_2$.

Clause 7: The compound of clause 5, wherein $R^3$ and $R^4$ are —$NH_2$.

Clause 8: The compound of clause 5, wherein $R^2$ and $R^3$ are —$NH_2$.

Clause 9: The compound of clause 5, wherein $R^2$ and $R^4$ are —$NH_2$.

Clause 10: The compound of clause 1, wherein three of $R^1$, $R^2$, $R^3$, and $R^4$ are —$NH_2$.

Clause 11: The compound of clause 10, wherein $R^1$, $R^3$ and $R^4$ are —$NH_2$.

Clause 12: The compound of clause 10, wherein $R^2$, $R^3$ and $R^4$ are —$NH_2$.

Clause 13: The compound of clause 1, wherein each of $R^1$, $R^2$, $R^3$, and $R^4$ are —$NH_2$.

Clause 14: A pharmaceutical composition comprising an effective amount of the compound of any one of clauses 1-13 or a pharmaceutically acceptable salt thereof, and a pharmaceutically acceptable carrier.

Clause 15: A method of treating an infection in a subject, comprising administering to the subject an effective amount of the pharmaceutical composition of clause 14.

Clause 16: The method of clause 15, wherein the infection is a fungal infection or a bacterial infection.

Clause 17: The method of clause 16, wherein the infection is a gram-positive bacterial infection.

Clause 18: The method of clause 16, wherein the infection is a gram-negative bacterial infection.

Clause 19: The method of clause 16, wherein the infection is a multi-drug resistant infection.

Clause 20: The method of any one of clauses 15-19, wherein the subject is a human.

What is claimed is:

1. A method of treating an infection comprising administering to a subject in need thereof a therapeutically effective amount of a compound of formula (I),

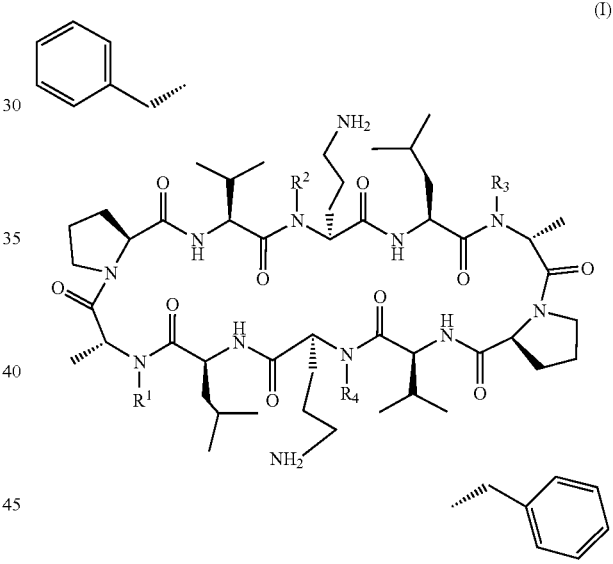

(I)

or a pharmaceutically acceptable salt thereof, wherein
$R^1$, $R^2$, $R^3$, and $R^4$ are each independently selected from hydrogen or —$NH_2$;
wherein at least one of $R^1$, $R^2$, $R^3$, and $R^4$ is —$NH_2$; and
wherein the infection is
a fungal infection caused by *Aspergillus, Candida, Coccidioides, Cryptococcus gatti, Pneumocystis jirovecii, Blastomyces, Cryptoccocus neoformans, Histoplasma*, or *Talaromyce*, or a combination thereof;
a gram-positive bacterial infection caused by *Actinomyces* spp.; *Aerococcus* spp.; *Bacillus* spp.; *Bacterionema* spp.; *Bifidobacterium* spp.; *Clostridium* spp.; *Corynebacterium* spp.; *Corprococcus* spp.; *Deinobacter* spp.; *Deinococcus* spp.; *Enterococcus* spp.; *Erysipelothrix* spp.; *Eubacterium* spp.; *Gemella* spp.; *Lactobacillus* spp.; *Lactococcus* spp.; *Leuconostoc* spp.; *Listeria* spp.; *Marinococcus* spp.;

*Melissococcus* spp.; *Methanobacterium* spp.; *Micrococcus* spp.; *Mycobacterium* spp.; *Micropolyspora* spp.; *Nocardia* spp.; *Pediococcus* spp.; *Peptococcus* spp.; *Peptostreptococcus* spp.; *Planococcus* spp.; *Propionibacterium* spp.; *Rothia* spp.; *Ruminococcus* spp.; *Saccharococcus* spp.; *Salinococcus* spp.; *Carcina* spp.; *Staphylococcus* spp.; *Stomatococcus* spp.; *Streptococcus* spp.; *Streptomyces* spp.; *Trichococcus* spp.; *Vagococcus* spp; or a combination thereof; or a gram-negative bacterial infection caused by *Acinetobacter* spp.; *Bacterioides* spp.; *Bordetella* spp.; *Borrelia* spp.; *Brucella* spp.; *Burkholderia* spp.; *Calymmatobacterium* spp.; *Campylobacter* spp.; *Chlamydia* spp.; *Chlamydophila* spp.; *Citrobacter* spp.; *Coxiella* spp.; *Edwardsiella* spp.; *Enterobacter* spp.; *Ehrlichia* spp.; *Escherichia* spp.; *Francisella* spp.; *Gardnerella* spp.; *Haemophilus* spp.; *Helicobacter* spp.; *Klebsiella* spp.; *Legionella* spp.; *Leptospira* spp.; *Moraxella* spp.; *Mycoplasma* spp.; *Neisseria* spp.; *Pasteurella* spp.; *Proteus* spp.; *Providencia* spp.; *Pseudomonas* spp.; *Rickettsia* spp.; *Salmonella* spp.; *Serratia* spp.; *Shigella* spp.; *Spirillaceae* spp.; *Streptobacillus* spp.; *Treponema* spp.; *Vibrio* spp.; *Yersinia* spp., or a combination thereof.

2. The method of claim 1, wherein $R^3$ is —$NH_2$.
3. The method of claim 1, wherein $R^4$ is —$NH_2$.
4. The method of claim 1, wherein two of $R^1$, $R^2$, $R^3$, and $R^4$ are —$NH_2$.
5. The method of claim 4, wherein Wand $R^3$ are —$NH_2$.
6. The method of claim 4, wherein $R^3$ and $R^4$ are —$NH_2$.
7. The method of claim 4, wherein $R^2$ and $R^3$ are —$NH_2$.
8. The method of claim 4, wherein $R^2$ and $R^4$ are —$NH_2$.
9. The method of claim 1, wherein three of $R^1$, $R^2$, $R^3$, and $R^4$ are —$NH_2$.
10. The method of claim 9, wherein $R^1$, $R^3$ and $R^4$ are —$NH_2$.
11. The method of claim 9, wherein $R^2$, $R^3$ and $R^4$ are —$NH_2$.
12. The method of claim 1, wherein each of $R^1$, $R^2$, $R^3$, and $R^4$ are —$NH_2$.
13. The method of claim 1, wherein the infection is a multi-drug resistant infection.
14. The method of claim 1, wherein the subject is a human.
15. The method of claim 1, wherein the infection is a fungal infection caused by *Aspergillus*, *Candida*, *Coccidioides*, *Cryptococcus gatti*, *Pneumocystis jirovecii*, *Blastomyces*, *Cryptoccocus neoformans*, *Histoplasma*, or *Talaromyce*, or a combination thereof.
16. The method of claim 1, wherein the infection is a gram-positive bacterial infection caused by a gram-positive bacterial infection caused by *Actinomyces* spp.; *Aerococcus* spp.; *Bacillus* spp.; *Bacterionema* spp.; *Bifidobacterium* spp.; *Clostridium* spp.; *Corynebacterium* spp.; *Corprococcus* spp.; *Deinobacter* spp.; *Deinococcus* spp.; *Enterococcus* spp.; *Erysipelothrix* spp.; *Eubacterium* spp.; *Gemella* spp.; *Lactobacillus* spp.; *Lactococcus* spp.; *Leuconostoc* spp.; *Listeria* spp.; *Marinococcus* spp.; *Melissococcus* spp.; *Methanobacterium* spp.; *Micrococcus* spp.; *Mycobacterium* spp.; *Micropolyspora* spp.; *Nocardia* spp.; *Pediococcus* spp.; *Peptococcus* spp.; *Peptostreptococcus* spp.; *Planococcus* spp.; *Propionibacterium* spp.; *Rothia* spp.; *Ruminococcus* spp.; *Saccharococcus* spp.; *Salinococcus* spp.; *Carcina* spp.; *Staphylococcus* spp.; *Stomatococcus* spp.; *Streptococcus* spp.; *Streptomyces* spp.; *Trichococcus* spp.; *Vagococcus* spp; or a combination thereof.

17. The method of claim 16, wherein the gram-positive bacterial infection is caused by *Enterococcus* spp., *Staphylococcus* spp., or a combination thereof.

18. The method of claim 1, wherein the infection is a gram-negative bacterial infection caused by *Acinetobacter* spp.; *Bacterioides* spp.; *Bordetella* spp.; *Borrelia* spp.; *Brucella* spp.; *Burkholderia* spp.; *Calymmatobacterium* spp.; *Campylobacter* spp.; *Chlamydia* spp.; *Chlamydophila* spp.; *Citrobacter* spp.; *Coxiella* spp.; *Edwardsiella* spp.; *Enterobacter* spp.; *Ehrlichia* spp.; *Escherichia* spp.; *Francisella* spp.; *Gardnerella* spp.; *Haemophilus* spp.; *Helicobacter* spp.; *Klebsiella* spp.; *Legionella* spp.; *Leptospira* spp.; *Moraxella* spp.; *Mycoplasma* spp.; *Neisseria* spp.; *Pasteurella* spp.; *Proteus* spp.; *Providencia* spp.; *Pseudomonas* spp.; *Rickettsia* spp.; *Salmonella* spp.; *Serratia* spp.; *Shigella* spp.; *Spirillaceae* spp.; *Streptobacillus* spp.; *Treponema* spp.; *Vibrio* spp.; *Yersinia* spp., or a combination thereof.

19. The method of claim 18, wherein the gram-negative bacterial infection is caused by *Acinetobacter* spp., *Enterobacter* spp., *Klebsiella* spp., *Pseudomonas* spp., or a combination thereof.

20. The method of claim 1, wherein the infection is a gram-positive bacterial infection caused by *Actinomyces israelii*; *Bacillus anthracis*; *Clostridium botulinum*; *Clostridium difficile*; *Clostridium perfringens*; *Clostridium tetani*; *Corynebacterium diphtherias*; *Enterococcus faecalis*; *Enterococcus faecium*; *Listeria monocytogenes*; *Mycobacterium avium*; *Mycobacterium leprae*; *Mycobacterium lepromatosis*; *Mycobacterium tuberculosis*; *Mycobacterium ulcerans*; *Nocardia asteroides*; *Staphylococcus aureus*; *Staphylococcus epidermidis*; *Staphylococcus saprophyticus*; *Streptococcus agalactiae*; *Streptococcus pneumoniae*; *Streptococcus pyogenes*; *Streptococcus viridans*; or a combination thereof; or a gram-negative bacterial infection caused by *Acinetobacter A. baumannii*; *Bacterioides fragilis*; *Bordetella pertussis*; *Borrelia burgdorferi*; *Borrelia garinii*; *Borrelia afzelii*; *Brucella abortus*; *Brucella canis*; *Brucella melitensis*; *Brucella suis*; *Burkholderia mallei*; *Burkholderia pseudomallei*; *Campylobacter fetus*; *Campylobacter jejuni*; *Chlamydia trachomatis*; *Chlamydia pneumoniae*; *Chlamydia psittaci*; *Chlamydophila pneumoniae*; *Coxiella burnetti*; *Ehrlichia canis*; *Ehrlichia chaffeensis*; *Escherichia coli*; *Francisella tularensis*; *Haemophilus influenzae*; *Helicobacter pylori*; *Klebsiella pneumoniae*; *Legionella pneumophila*; *Leptospira interrogans*; *Moraxella catarrhalis*; *Mycoplasma pneumoniae*; *Neisseria gonorrhoeae*; *Neisseria meningitidis*; *Pseudomonas aeruginosa*; *Pseudomonas mallei*; *Rickettsia akari*; *Rickettsia prowazekii*; *Rickettsia rickettsia*; *Salmonella enterica*; *Salmonella enterica enteritidis*; *Salmonella enterica hadar*; *Salmonella enterica Heidelberg*; *Salmonella enterica infantis*; *Salmonella enterica paratyphi*; *Salmonella enterica typhi*; *Salmonella enterica typhimurium*; *Shigella dysenteriae*; *Shigella sonnei*; *Spirillaceae minus*; *Streptobacillus moniliformis*; *Treponema pallidum*; *Vibrio cholerae*; *Yersinia enterocolitica*; *Yersinia pestis*; *Yersinia pseudotuberculosis*; or a combination thereof.

* * * * *